United States Patent
Subramanian

(10) Patent No.: US 11,406,800 B2
(45) Date of Patent: Aug. 9, 2022

(54) MULTI-PURPOSE BALLOON CATHETER FOR INTRA CAVITY RADIATION DELIVERY

(71) Applicant: Best Medical International, Inc., Springfield, VA (US)

(72) Inventor: Manny R. Subramanian, Frederick, MD (US)

(73) Assignee: Best Medical International, Inc., Springfield, VA (US)

( * ) Notice: Subject to any disclaimer, the term of this patent is extended or adjusted under 35 U.S.C. 154(b) by 122 days.

(21) Appl. No.: 16/801,325

(22) Filed: Feb. 26, 2020

(65) Prior Publication Data
US 2020/0197672 A1 Jun. 25, 2020

Related U.S. Application Data

(60) Division of application No. 15/292,923, filed on Oct. 13, 2016, now Pat. No. 10,744,307, which is a
(Continued)

(51) Int. Cl.
*A61M 25/10* (2013.01)
*A61N 5/10* (2006.01)
(Continued)

(52) U.S. Cl.
CPC .......... *A61M 25/1011* (2013.01); *A61M 1/84* (2021.05); *A61M 25/0017* (2013.01);
(Continued)

(58) Field of Classification Search
CPC ............... A61M 25/1011; A61M 1/84; A61M 25/0017; A61M 25/10181;
(Continued)

(56) References Cited

U.S. PATENT DOCUMENTS 2,799,273 A 7/1957 Oddo
4,976,266 A 12/1990 Huffman et al.
(Continued)

FOREIGN PATENT DOCUMENTS

JP 2009232882 10/2009
WO 99/27985 6/1999
(Continued)

OTHER PUBLICATIONS

Astro 2015 Annual Meeting, Ancer Medical, Hialeah, FL Booth 489, Print Profile, Oct. 2015, 2 pages.
(Continued)

*Primary Examiner* — Navin Natnithithadha
*Assistant Examiner* — Sunita Reddy
(74) *Attorney, Agent, or Firm* — John C. Brosky; JanPaul Guzman

(57) ABSTRACT

A multi-purpose balloon catheter includes a catheter having a proximal end portion, a central portion and a non-branching distal end portion, a plurality of lumens associated with the catheter extending from the proximal end portion, and a plurality of inflatable balloons positioned in the central portion and/or the non-branching distal end portion. Each of the plurality of inflatable balloons is communicatively associated with a corresponding one of the plurality of lumens, the plurality of inflatable balloons being selectively inflated or deflated to position and stabilize the catheter in a cavity for delivery of a medical treatment. The catheter can include an extraction point associated with a lumen to remove fluids and materials from the cavity, and a connector associated with a corresponding lumen adapted to selectively receive one or more of a fluid medium or a radioactive isotope provided to a corresponding lumen for delivery of the medical treatment.

20 Claims, 15 Drawing Sheets

Related U.S. Application Data continuation-in-part of application No. 15/189,396, filed on Jun. 22, 2016, now Pat. No. 10,406,381, which is a division of application No. 12/889,032, filed on Sep. 23, 2010, now Pat. No. 9,402,980.

(60) Provisional application No. 62/242,976, filed on Oct. 16, 2015.

(51) Int. Cl.
| | | |
|---|---|---|
| *A61M 1/00* | (2006.01) | |
| *A61M 25/00* | (2006.01) | |
| *A61M 31/00* | (2006.01) | |

(52) U.S. Cl.
CPC .... *A61M 25/0026* (2013.01); *A61M 25/1002* (2013.01); *A61M 25/10181* (2013.11); *A61M 31/005* (2013.01); *A61N 5/1002* (2013.01); *A61N 5/1014* (2013.01); *A61N 5/1015* (2013.01); *A61N 5/1016* (2013.01); *A61N 5/1071* (2013.01); *A61M 2025/105* (2013.01); *A61M 2025/1045* (2013.01); *A61M 2210/105* (2013.01); *A61M 2210/1064* (2013.01); *A61M 2210/1067* (2013.01); *A61M 2210/1089* (2013.01); *A61M 2210/1475* (2013.01); *A61N 2005/1003* (2013.01); *A61N 2005/1004* (2013.01); *A61N 2005/1018* (2013.01); *A61N 2005/1021* (2013.01); *A61N 2005/1024* (2013.01); *A61N 2005/1025* (2013.01)

(58) Field of Classification Search
CPC .......... A61M 25/1002; A61M 25/0026; A61M 31/005; A61M 2025/105; A61M 2025/1045; A61M 2210/1089; A61M 2210/1067; A61M 2210/1475; A61M 2210/1064; A61M 2210/105; A61N 5/1071; A61N 5/1002; A61N 5/1016; A61N 5/1015; A61N 5/1014; A61N 2005/1004; A61N 2005/1018; A61N 2005/1003; A61N 2005/1025; A61N 2005/1024; A61N 2005/1021
USPC .......................................................... 600/1–8
See application file for complete search history.

(56) References Cited

U.S. PATENT DOCUMENTS

| | | | |
|---|---|---|---|
| 5,623,940 | A | 4/1997 | Daikuzono |
| 5,653,683 | A | 8/1997 | D'Andrea |
| 5,720,717 | A | 2/1998 | D'Andrea |
| 5,782,800 | A | 7/1998 | Yoon |
| 5,913,813 | A | 6/1999 | Williams et al. |
| 6,119,697 | A | 9/2000 | Engel et al. |
| 6,165,199 | A | 12/2000 | Barbut |
| 6,251,059 | B1 | 6/2001 | Apple et al. |
| 6,258,019 | B1 | 7/2001 | Verin et al. |
| 6,398,708 | B1 | 6/2002 | Hastings et al. |
| 6,398,709 | B1 | 6/2002 | Ehr et al. |
| 6,447,462 | B1 | 9/2002 | Wallace et al. |
| 6,616,629 | B1 | 9/2003 | Verin et al. |
| 6,923,754 | B2 | 8/2005 | Lubock |
| 6,955,641 | B2 | 10/2005 | Lubock |
| 6,958,052 | B1 | 10/2005 | Charlton |
| 7,184,827 | B1 | 2/2007 | Edwards |
| 7,357,770 | B1 | 4/2008 | Cutrer et al. |
| 7,662,082 | B2 | 2/2010 | White et al. |
| 8,251,884 | B2 | 8/2012 | Lubock et al. |
| 8,277,370 | B2 | 10/2012 | Quick |
| 8,287,442 | B2 | 10/2012 | Quick |
| 8,348,825 | B2 | 1/2013 | Partridge et al. |
| 8,360,950 | B2 | 1/2013 | Acosta et al. |
| 8,568,284 | B2 | 10/2013 | White et al. |
| 8,961,383 | B2 | 2/2015 | Parsai et al. |
| 9,283,402 | B2 | 3/2016 | Cutrer |
| 9,402,980 | B2 | 8/2016 | Subramanian |
| 9,498,644 | B2 | 11/2016 | Cutrer |
| 9,895,253 | B2 | 2/2018 | Giap et al. |
| 10,406,381 | B2 | 9/2019 | Subramanian |
| 2003/0032851 | A1 | 2/2003 | Apple et al. |
| 2004/0087827 | A1 | 5/2004 | Lubock |
| 2005/0027157 | A1 | 2/2005 | Winkler et al. |
| 2005/0080313 | A1 | 4/2005 | Stewart et al. |
| 2005/0101824 | A1 | 5/2005 | Stubbs |
| 2005/0182286 | A1 | 8/2005 | Lubock |
| 2006/0100475 | A1 | 5/2006 | White et al. |
| 2006/0173233 | A1 | 8/2006 | Lovoi |
| 2006/0212002 | A1 | 9/2006 | Fangrow, Jr. |
| 2006/0212022 | A1 | 9/2006 | Gellman |
| 2007/0106108 | A1 | 5/2007 | Hermann et al. |
| 2007/0142695 | A1 | 6/2007 | White et al. |
| 2007/0167666 | A1 | 7/2007 | Lubock et al. |
| 2008/0215031 | A1 | 9/2008 | Belfort et al. |
| 2008/0221384 | A1 | 9/2008 | Chi Sing et al. |
| 2008/0281143 | A1 | 11/2008 | Lubock et al. |
| 2009/0082609 | A1 | 3/2009 | Condado |
| 2009/0143634 | A1 | 6/2009 | Benson et al. |
| 2009/0156880 | A1 | 6/2009 | Allan et al. |
| 2009/0198095 | A1 | 8/2009 | Acosta et al. |
| 2009/0209805 | A1 | 8/2009 | Lubock et al. |
| 2009/0254064 | A1 | 10/2009 | Boatman |
| 2009/0264696 | A1 | 10/2009 | White et al. |
| 2009/0306453 | A1 | 12/2009 | Popowski et al. |
| 2009/0312593 | A1 | 12/2009 | Drobnik et al. |
| 2009/0318855 | A1 | 12/2009 | Ehrenreich |
| 2010/0069878 | A1 | 3/2010 | Parsi et al. |
| 2010/0191034 | A1 | 7/2010 | Cutrer et al. |
| 2010/0204688 | A1 | 8/2010 | Hoey et al. |
| 2010/0331601 | A1 | 12/2010 | Partridge et al. |
| 2011/0034976 | A1 | 2/2011 | Mon et al. |
| 2011/0152683 | A1 | 6/2011 | Gerrans et al. |
| 2011/0230700 | A1 | 9/2011 | Sing et al. |
| 2012/0022314 | A1* | 1/2012 | Sing .................... A61N 5/1027 600/3 |
| 2012/0172651 | A1 | 7/2012 | Cutrer |
| 2012/0253099 | A1 | 10/2012 | Mon et al. |
| 2013/0030411 | A1 | 1/2013 | Kreck |
| 2014/0005539 | A1 | 1/2014 | Forster et al. |
| 2014/0066896 | A1 | 3/2014 | Tilson et al. |
| 2014/0257092 | A1 | 9/2014 | Lamoureux et al. |
| 2014/0275712 | A1 | 9/2014 | D'Andrea |
| 2014/0277466 | A1 | 9/2014 | Teisen et al. |
| 2016/0045212 | A1* | 2/2016 | Janardhan ........ A61B 17/22031 606/200 |
| 2017/0028174 | A1 | 2/2017 | Subramanian |
| 2017/0035997 | A1 | 2/2017 | Subramanian |
| 2017/0333075 | A1* | 11/2017 | Bacino ............ A61M 25/10184 |
| 2019/0053935 | A1 | 2/2019 | Giap et al. |
| 2019/0117519 | A1 | 4/2019 | Schmid-Schonbein |
| 2020/0171284 | A1 | 1/2020 | Subramanian |
| 2020/0171285 | A1 | 2/2020 | Subramanian |
| 2020/0306511 | A1 | 6/2020 | Subramanian |
| 2020/0338321 | A1 | 10/2020 | Subramanian |

FOREIGN PATENT DOCUMENTS

| | | |
|---|---|---|
| WO | 2008124149 | 10/2008 |
| WO | 2013049827 | 4/2013 |

OTHER PUBLICATIONS

Gilad N. Cohen et al., "Design of a Novel Applicator for Esophageal High Dose Rate Brachytherapy", Abstract P051, Abstracts / Brachytherapy, vol. 14, 2015, pp. S101-S102.
"Whal is Esophageal Brachytherapy" Ancer Medical, Available at http://www.ancermedical.com/wp-conlenl/ uploads/2016/04/ Esophageal-Applicalor.pdf, 2016, 6 pages.
Esophageal Applicator (E-App™), Ancer Medical, 2016, 1 page.
Anorectal Applicator (AR)™, Ancer Medical, 2016, 2 pages.

(56) References Cited

OTHER PUBLICATIONS

Esophageal Applicator (E-App)™, Ancer Medical, Available at http://www.ancermedical.com/wp-conlenl/ uploads/2016/04/Esophageal-Applicalor.pdf, 2016, 5 pages.
"Hologic takes SenoRx assets in out-of-court settlement with C.R. Bard", A. Sarvestani, www.massdevice.com, Aug. 14, 2013 (downloaded, Oct. 19, 2015), 4 pages.
"Best Dual Balloon Breast Brachytherapy Applicator", from TeamBest brochure/material, Sep. 13, 2014, 3 pages.

* cited by examiner

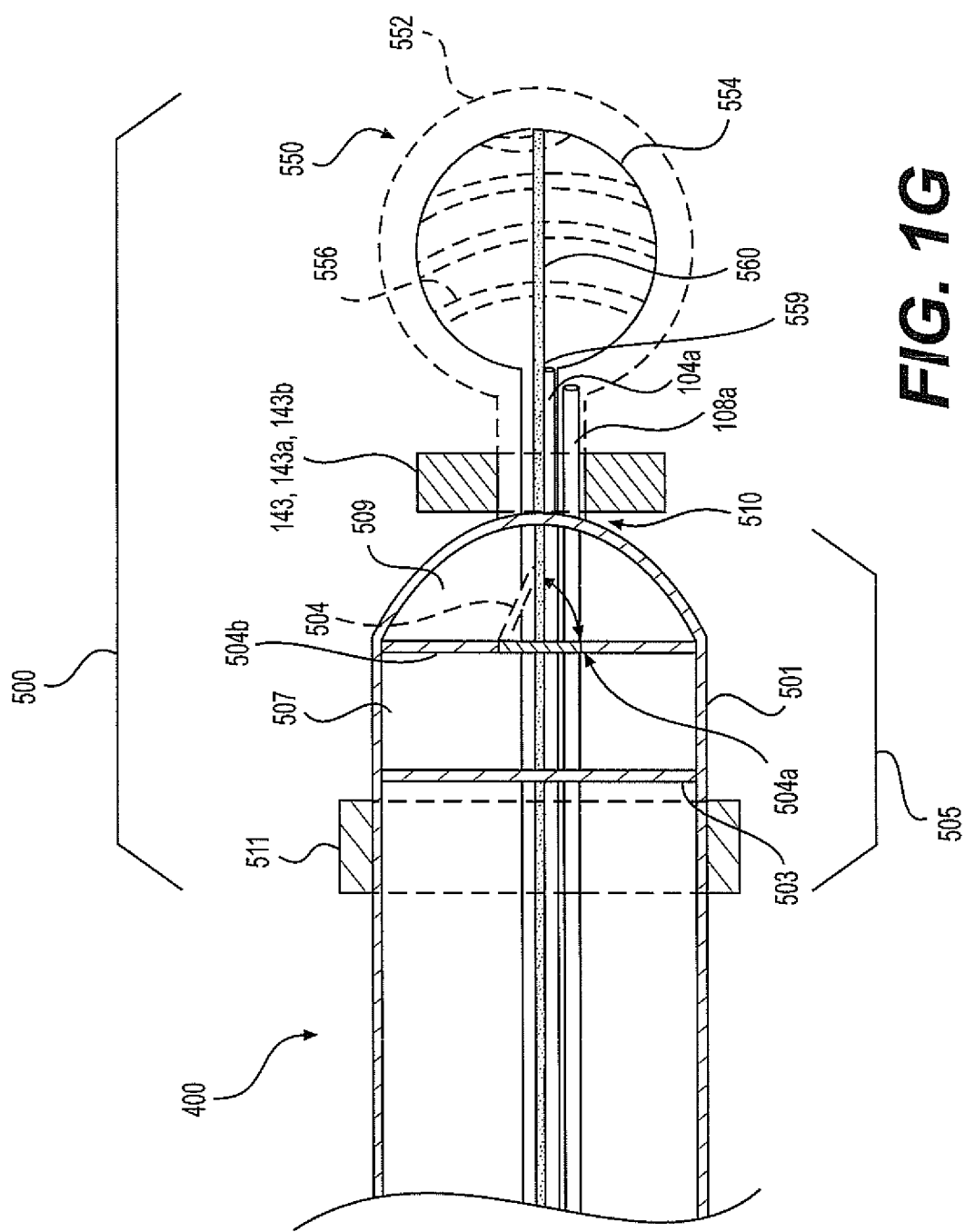

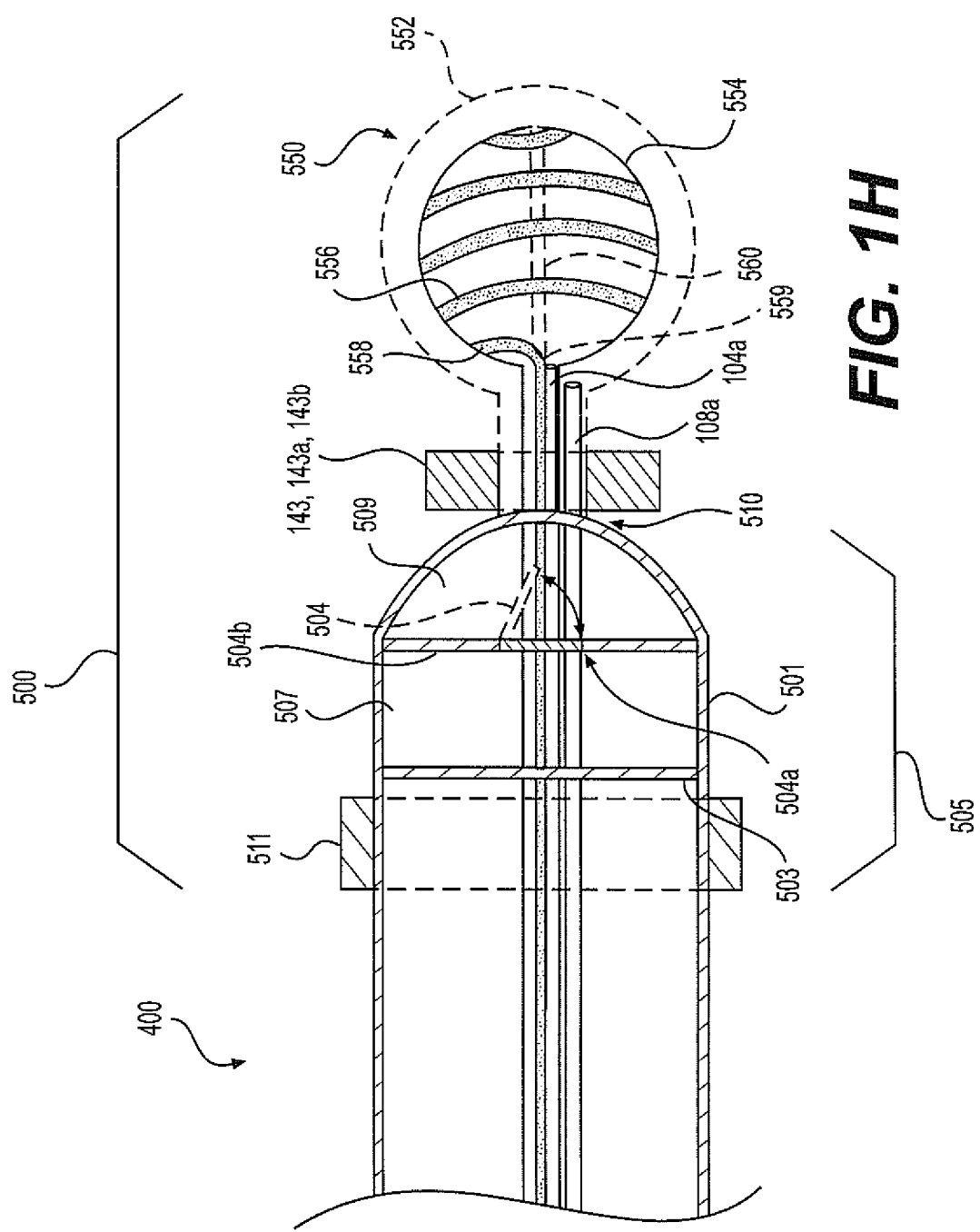

MULTI-PURPOSE BALLOON CATHETER FOR INTRA CAVITY RADIATION DELIVERY

CROSS-REFERENCE TO RELATED APPLICATIONS

This application claims priority under 35 U.S.C. § 120 to and is a divisional application of U.S. patent application Ser. No. 15/292,923, filed on Oct. 13, 2016, now issued as U.S. Pat. No. 10,744,307, which claims priority under 35 U.S.C. § 120 to and is a continuation-in-part (CIP) of U.S. patent application Ser. No. 15/189,396, filed on Jun. 22, 2016, now issued as U.S. Pat. No. 10,406,381, which claims priority under 35 U.S.C. § 120 to and is a divisional application of U.S. patent application Ser. No. 12/889,032, filed on Sep. 23, 2010, now issued as U.S. Pat. No. 9,402,980, and U.S. patent application Ser. No. 15/292,923 also claims priority under 35 U.S.C. § 119 to U.S. Provisional Patent Application No. 62/242,972, filed on Oct. 16, 2015, all of which are hereby incorporated by reference in their entirety.

FIELD OF THE INVENTION

The invention generally relates to medical devices, and more particularly to a multi-purpose balloon catheter having a plurality of balloons for selectively stabilizing and positioning the catheter, for delivering a radiation dose, for measuring and imaging internal organs, cavities, and removing bodily fluids or material while providing an easy connection module for treatment.

BACKGROUND

A catheter is a tube that can be inserted into a body cavity, duct, or vessel. Catheters thereby allow drainage, injection of fluids, or access by surgical instruments. The process of inserting a catheter is catheterization. In most uses, a catheter is a thin, flexible tube ("soft" catheter), though in some uses, it is a larger, solid ("hard") catheter. A catheter left inside the body, either temporarily or permanently, may be referred to as an indwelling catheter. A permanently inserted catheter may be referred to as a Permcath®, for example.

The ancient Syrians created catheters from reeds. "Katheter—καθετηρ" originally referred to an instrument that was inserted such as a plug. The word "katheter" in turn came from "kathiemai—ηαθιεμαι" meaning "to sit". The ancient Greeks inserted a hollow metal tube through the urethra into the bladder to empty it and the tube came to be known as a "katheter".

Heretofore various balloon type catheters and perfusion catheters have been proposed for performing one or two procedures. However, heretofore, prior to the present invention, a multi-purpose balloon catheter capable of performing two or more procedures has not been available.

The incidence of esophageal and stomach cancers continue to increase globally. Often patients die without proper diagnosis and/or treatment. For localized cancers, tumors can be first shrunk with the help of high dose rate brachytherapy employing appropriate applicators. This can be followed by surgical, chemotherapeutic and/or biological agents or mediated targeted therapeutic procedures. Positioning and targeting of radiation to the site of disease with minimal or no damage to normal nearby organs remains a challenge. Thus, the need exists to have a catheter that can not only provide multiple functions but also can be selectively positioned and targeted for delivering the radiation or other suitable treatment modalities and other applications such as rectal, bladder, colon, uteral, cervical and breast cancers. The catheters of the present invention can address that need as well as can promote minimizing risk of causing damage to surrounding tissue or can promote reducing pain during a treatment procedure.

Thus, a multi-purpose balloon catheter for intra cavity radiation delivery addressing the aforementioned problems is desired.

SUMMARY OF INVENTION

A multi-purpose balloon catheter includes a single intra-cavity catheter having a proximal end portion, a central portion and a non-branching distal end portion, a plurality of lumens positioned in association with the catheter extending from the proximal end portion, and a plurality of inflatable balloons arranged in a plurality of independent and distinct balloon groups. Each of the plurality of inflatable balloons are positioned in association with one or more of the central portion and/or the non-branching distal end portion of the single intra-cavity catheter. Each of the plurality of inflatable balloons is communicatively connected to a corresponding one of the plurality of lumens, the plurality of inflatable balloons being selectively inflated or deflated to position and/or stabilize the catheter in a cavity for delivery of a medical treatment or selectively filled with a treatment medium, such as a radioactive material, or a contrast medium, for delivery of the medical treatment.

The multi-purpose balloon catheter can include a secondary treatment balloon positioned at the non-branching distal end portion of the single intra-cavity catheter and communicatively connected to one or more of the plurality of lumens, and at least one of the plurality of lumens is adapted to provide a medium to selectively inflate or deflate the secondary treatment balloon to selectively position and/or stabilize the secondary treatment balloon for delivery of the medical treatment and another of the plurality of lumens adapted to deliver a radioactive dose or a therapeutic agent or therapeutic medium for the medical treatment. In addition, a radioactive wire can be inserted into one of the lumens to deliver radiation to an internal organ or cavity of a patient. The multi-purpose balloon catheter can further include a marker placed in association with the non-branching distal end portion of the single intra-cavity catheter to indicate a position of the catheter.

These and other features of the present invention will become readily apparent upon further review of the following specification and drawings.

DESCRIPTION OF THE DRAWINGS

FIG. 1G is another embodiment of an applicator extender in conjunction with an embodiment of a treatment balloon that can be fitted in association with the distal end portion of the embodiment of the catheter of FIG. 1E, or that can be fitted in association with the distal end portion of the embodiment of the catheter of FIG. 1A.

FIG. 1H is a further embodiment of an applicator extender in conjunction with an embodiment of a treatment balloon that can be fitted in association with the distal end portion of the embodiment of the catheter of FIG. 1E, or that can be fitted in association with the distal end portion of the embodiment of the catheter of FIG. 1A.

Unless otherwise indicated, similar reference characters denote corresponding features consistently throughout the attached drawings.

DETAILED DESCRIPTION

The present disclosure relates to a multi-purpose balloon catheter for delivering a medical treatment, such as radiation, and for targeting single to multiple disease sites with a novel multi-balloon configuration. Additionally, the multi-purpose balloon catheter enables fixing or positioning radioactive wires or radioactive material in a cavity, such as in the esophagus, in other organs or in a surgically created cavity, to deliver the medical treatment, such as radiation or a therapeutic agent to a targeted portion of an organ or surgically created cavity using a conformable device including balloons, lumens and a single intra-cavity catheter. Moreover, the multi-purpose balloon catheter allows for diagnosing the anatomy of an abnormal organ shape by evaluating the balloon shape (with contrast agent) by comparing to shapes of normal healthy patient organs. The multi-purpose balloon catheter allows for the medical treatment of multiple sites with diseases using the same device (esophageal and stomach cancers). Finally, the multi-purpose balloon catheter allows for the medical treatment of one organ while determining the dose delivered to a nearby normal organ with a small dosimeter (MOSFET system).

Figure 1A:
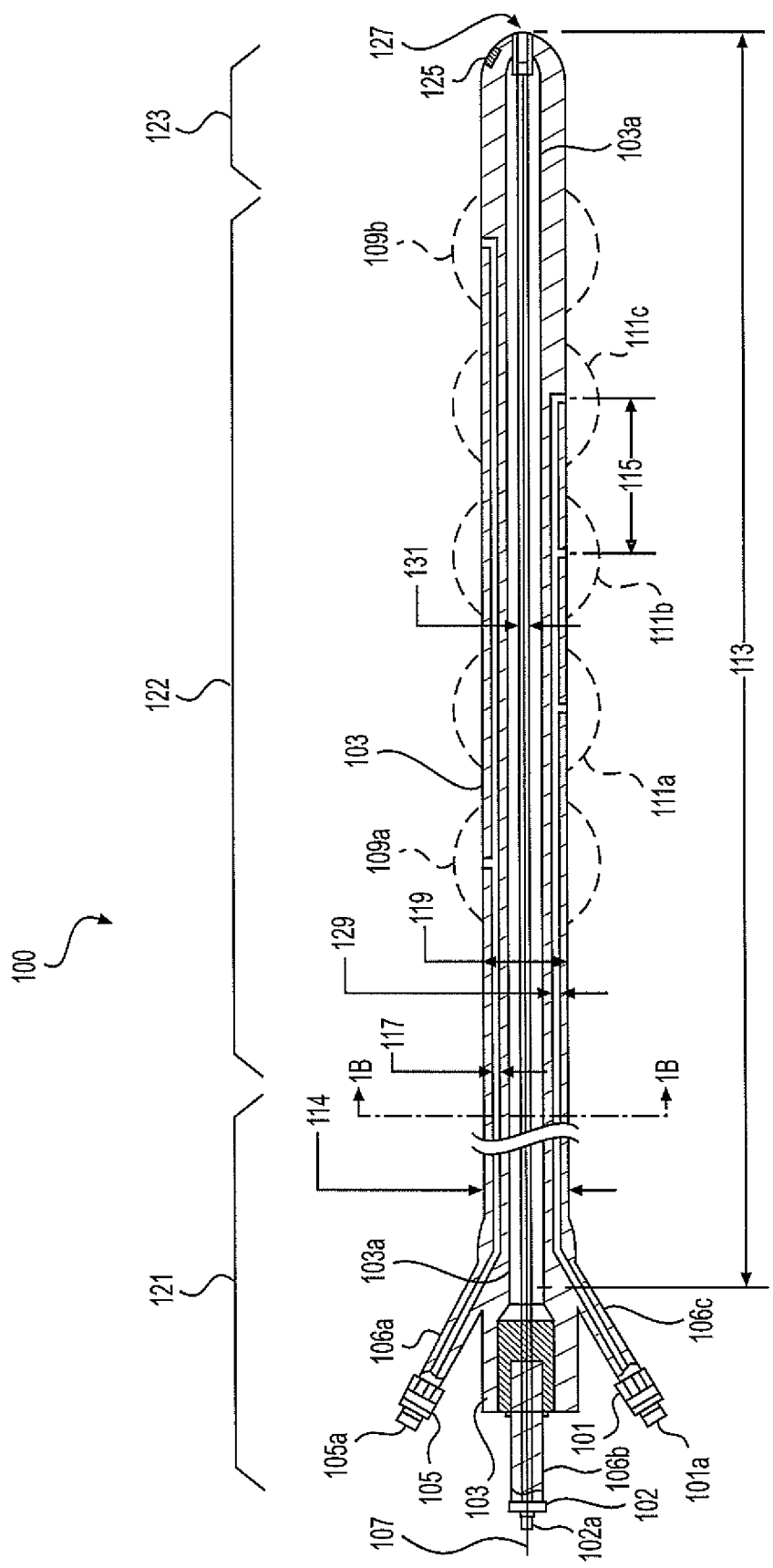
FIG. 1A is a longitudinal plan view of an embodiment of a multi-purpose balloon catheter according to the present invention.

Referring now to the drawings in greater detail, there is illustrated in FIG. 1A, an embodiment of a multi-purpose balloon catheter 100 according to the teachings of the invention. The multi-purpose balloon catheter 100 includes a proximal end portion 121, a central portion 122 having, for example, a generally tubular shaped body 103, and a non-branching distal end portion 123, with the non-branching distal end portion 123 including a suitable marker such as a X-ray marker 125 to indicate a position of the non-branching distal end portion 123 of the multi-purpose balloon catheter 100. The X-ray marker 125 typically can be gold, lead, tungsten or other heavy metal suitable for X-ray visualization, or can be other suitable material, as can depending on the use or application, and should not be construed in a limiting sense.

The multi-purpose balloon catheter 100 can be made of various suitable materials, such as a polymeric material, such as a polyurethane or a polyacrylic material, among other examples, depending on the use or application, for example. Typically, a length 113 of the multi-purpose balloon catheter 100 of FIG. 1A is about 78 cm to the tip from the base area of the multi-purpose balloon catheter 100, but the catheter 100 can be of various suitable lengths and dimensions, depending on the use or application, for example. A diameter 114 of the catheter 100 of FIG. 1A is typically 0.45 cm, but can be of various suitable diameters, depending on the use or application, for example.

The proximal end portion 121 of the catheter 100 includes the plurality of neck portions 106a, 106b, and 106c, made of similar suitable material as the catheter 100. The neck portions 106a, 106b, and 106c each include a corresponding lumen 101a, 102a and 105a therein that extends within the catheter 100 for balloon inflation or for the delivery of the medical treatment, for example. The central lumen 102a is coaxially positioned within the central portion 122 of the catheter 100 extending longitudinally through the catheter 100 to the non-branching distal end portion 123. The neck portions 106a, 106b, and 106c and corresponding lumens 101a, 102a and 105a are desirably associated with a corresponding suitable connector or connecting mechanism 101, 102 and 105, such as suitable luer locks 101, 102, and 105, that can be a male or a female connection, for example.

For example, the luer-locks 101 and 105 can be fitted with syringes for selectively inflating balloons 111a, 111b, and 111c and balloons 109a and 109b to a predetermined size, for a particular use or application, for example. The balloons 111a, 111b, and 111c and the balloons 109a and 109b being desirably located in the central portion 122 to facilitate positioning and stabilizing the catheter 100 for delivery of a the medical treatment. In the catheter 100, the lumen 101a associated with the luer lock 101 can receive and remove a fluid medium, such as saline solution or a gaseous medium, such as by a syringe or other suitable delivery mechanism, such as a pump, to selectively inflate or deflate the balloons 111a, 111b, and 111c.

Similarly, the lumen 105a associated with the luer lock 105 can receive and remove a fluid medium, such as saline solution or a gaseous medium, such as by a syringe or other suitable delivery mechanism, such as a pump, to selectively inflate or deflate the balloons 109a and 109b, for example. The locking mechanism or connector, such as provided by the luer locks 101, 102 and 105, when affixed to the catheter 100 can provide for selectively not allowing or selectively allowing a fluid medium, such as including fluids, fluid or gaseous mediums, such as air, or allowing a contrast medium, for example, to pass through a corresponding connecting point provided by the connector or connecting mechanism 101, 102 and 105, such as luer locks, of the catheter 100.

As depicted in FIG. 1A, the central lumen 102*a* associated with the connector 102, such as a luer lock, can be used to insert a radioactive wire 107 as a radiation source or a radioactive material into the treatment catheter 100, such radiation source or radioactive material can also include a radioactive seed for the delivery of the medical treatment at a specific site or at a predetermined location of the organ or cavity. Also, the central lumen 102*a* associated with the locking mechanism or connector 102, such as a luer lock, can be used with suction or a syringe to remove bodily fluids or material from a cavity in a body, such as an area adjacent to the cavity, using the treatment catheter 100, such as by communicating with an extraction opening 127 at the non-branching distal end portion 123 of the catheter 100, such as illustrated in FIG. 1A, for example. The central lumen 102*a* can be positioned in a larger main lumen 103*a* extending through the catheter 100, as illustrated in FIG. 1A. The locking mechanism or connector 102 for the lumen 102*a* can allow for a relatively easier controlled delivery and guidance for the medical treatment or extraction within a treatment area, for example.

Selectively inflating the balloons 109*a*, 109*b*, 111*a*, 111*b* and 111*c* can allow for selectively positioning and/or stabilizing the catheter 100 or for administration of the medical treatment or for removal of bodily fluids or material in a cavity, such as in a bodily organ or in a cavity region, such as the esophagus, rectum, stomach or a surgically created cavity, such as in the breast or other organ or bodily tissue, such as through the lumen 102*a*, for example. The lumens 101*a* and 105*a* and the inflated balloons 109*a*, 109*b*, 111*a*, 111*b* and 111*c* can contain a contrast liquid or other contrast medium, such as for contrast purposes in imaging applications, that can also be used for inflation of the balloons 109*a*, 109*b*, 111*a*, 111*b* and 111*c*, for positioning, stabilization and treatment, for example. As illustrated in FIG. 1A, the balloons 109*a*, 109*b*, 111*a*, 111*b* and 111*c* can be arranged in a plurality of independent and distinct balloon groups in association with the central portion 122 of the catheter 100. For example, as illustrated in FIG. 1A, the balloons 109*a* and 109*b* can form a first balloon group, and the balloons 111*a*, 111*b* and 111*c* can form a second balloon group. Each independent and distinct balloon group can be selectively inflated or deflated or can also receive and can have removed a contrast liquid or other contrast medium independently of the balloons of another balloon group, such as through corresponding ones of the plurality of connectors, such as connectors 101 and 105, and through the associated corresponding ones of the plurality of the lumens, such as lumens 101*a* and 105*a*, for example.

As discussed herein, the catheter 100 includes a plurality of balloons, such as the balloons 109*a*, 109*b*, 111*a*, 111*b* and 111*c* that may be arranged in a plurality of independent and distinct balloons groups, such as the first balloon group including balloons 109*a* and 109*b* and the second balloon group including balloons 111*a*, 111*b*, and 111*c*. The lumens of the catheter 100, such as the lumens 101*a* and 105*a*, can be communicatively connected to a single or to any of various pluralities of balloons. For example, the lumen 101*a* can be connected with balloons 111*a*, 111*b*, 111*c* of the second balloon group and the lumen 105*a* can be connected to balloons 109*a* and 109*b* of the first balloon group, as illustrated in FIG. 1A, for example. Also, the catheter 100 can have any of various other suitable connection arrangements with more or less lumens or balloons, depending on the use or application, for example. Further, the balloons, such as the balloons 109*a*, 109*b*, 111*a*, 111*b* and 111*c*, can have any of various suitable sizes or shapes, such as cylindrical, spherical, oval, oblong, toroidal, or other suitable shapes, depending on the use or application, for example.

The lumens, such as the lumens 101*a*, 102*a* and 105*a*, can have any of various suitable sizes, shapes or configurations, such as cylindrical, rectangular, oval, or other suitable shapes or configurations, depending on the use or application, for example. Also, a typical dimension of a diameter of the lumens, such as indicated at 117 for diameter of the lumen 105*a*, as indicated at 129 for a diameter of the lumen 101*a*, and as indicated at 131 for a diameter of the lumen 102*a*, for inflating the balloons 109*a*, 109*b*, 111*a*, 111*b* and 111*c* and/or for delivery of the medical treatment, can be typically in a range of from about 0.8 mm to about 1.5 mm, for example, but can be of various suitable dimensions, depending on the use or application, and should not be construed in a limiting sense.

Further, the spacing between each of the centers of adjacent ones of the balloons 109*a*, 109*b*, 111*a*, 111*b* and 111*c*, desirably corresponding to the spacing between adjacent exit points of the lumens 101*a* and 105*a* of respective adjacent balloons, can be a same or a different spacing, depending on the use or application, such as desirably being spaced apart by about 2.5 cm from each other as indicated at 115, for example. The first balloon group including the balloons 109*a* and 109*b* is independently arranged from the second balloon group including the balloons 111*a*, 111*b* and 111*c* on the catheter 100 along the length 113 of the catheter 100, such as illustrated in FIG. 1A. Also, the lumens, such as the lumens 101*a*, 102*a* and 105*a*, can be positioned within an interior of the catheter 100, such interior of the catheter 100 being indicated by the numeral 119, or can be positioned or integrally formed on or in an exterior surface or layer of the catheter 100, for example, depending on the use or application, for example.

The balloons, such as the balloons 109*a*, 109*b*, 111*a*, 111*b* and 111*c*, can be made of nylon, polyurethane, Polyether block amide Pebax®, poly(ethylene terephthalate), commonly abbreviated PET or other thermoplastic elastomers or other suitable materials, depending on the use or application, for example. Additionally, one or more of the balloons 109*a*, 109*b*, 111*a*, 111*b* and 111*c* and all or part of the catheter 100, such as the body 103 of the central portion 122 of the catheter 100, can be coated or impregnated with various suitable coatings for ease of assembly such as a silicone type coating, or the balloons can be impregnated or coated with various suitable therapeutic or medicinal agents for treatment at a site within the body, such as by elution of the agent from the balloon or the catheter, for example.

In an embodiment, the catheter 100, as well as the balloons associated with the catheter 100, such as the balloons 109*a*, 109*b*, 111*a*, 111*b*, and 111*c*, can be uncoated or can be coated with a lubricant for lubrication for ease of positioning the catheter 100 at a treatment site, or can be coated or formed with antimicrobial or medicinal agents for delivery of the medical treatment at the treatment site, for example. In this regard, in various embodiments of catheters, such as the catheter 100, various therapeutic drugs can be coated onto the surface of the balloons or catheter for releasing the drug internally to a specific location of the cavity being treated.

The catheter 100 of FIG. 1A having a plurality of connectors or locking mechanisms, such as the luer-locks 101, 102 and 105 as examples of connectors or locking mechanisms, and a plurality of balloons, such as the balloons 109a, 109b, 111a, 111b, and 111c, can be inserted into various body cavities, such as the esophagus, but is not limited thereto and can also be inserted for the medical treatment into other cavities, such as the rectum, vagina, etc. or surgically created cavities, wherein the radioactive wire, radioactive seed or other radioactive or therapeutic material or other therapeutic agent, can provide the requisite radiation dose or therapeutic agent to treat cancerous growth or other medical conditions. Typically, the dimension of the radioactive wire, such as the radioactive wire 107, that can be inserted into the lumen 102a, is desirably in a range of about 0.5 mm to about 0.8 mm, for example, but can be of various suitable dimensions and configurations, depending on the use or application.

Desirably, the radioactive wire, such as the radioactive wire 107, is made of a suitable radioactive material, such as Iridium-192, Cobalt 60 and Yttrium 168, for example. The high dose rate (HDR) treatment delivered through the catheter, such as the catheter 100, can be conducted with Ir-192, Au-198, I-125 and Cs-131, for example. Typically the dose of radiation delivered by the radioactive wire, such as the radioactive wire 107, is about 1 Curie to about 10 Curies per seed, but can be any suitable dose, depending on the use or application. Also, HDR afterloaders can be used in conjunction with embodiments of the catheters, such as the catheter 100, for the delivery of a radiation dose for the medical treatment, such as Varisource, Gamma Med and BEBIG afterloaders or other suitable afterloaders, for example.

For a low dose rate (LDR) application delivered through embodiments of catheters, such as the catheter 100, Sr-90 can be used in conjunction with the radiation wire, such as the radioactive wire 107, as well as Cs-131 and Yb-168 can also be used as the radiation source, for example. Typically the dose of radiation using the LDR configuration is usually one thousand times less than the HDR applications, such LDR dose being in a range of about 1 milli Curie to about 10 milli Curies, for example.

An advantage, among others, of embodiments of catheters, such as the catheter 100, is that it can allow for delivering the radiation dose to a specific or a predetermined site or location of or in the cavity, such as in an organ, a body cavity or a surgically created cavity, such as by the radioactive wire 107, through the lumen 102a, and can also allow, at the same time or at different times, for the removal of fluid or bodily material, from the area of the treatment site, such as through the lumen 102a or the main lumen 103a, for example, while also providing enhanced stabilization and positioning of the catheter, such as the catheter 100, for the medical treatment, by selective inflation or deflation of the corresponding balloons, such as the balloons 109a, 109b, 111a, 111b, and 111c, for example, that can allow selectively controlling the size of each balloon independently or in conjunction with one or more other balloons, to selectively adjust the location and positioning of the catheter at the treatment site.

Figure 1B:
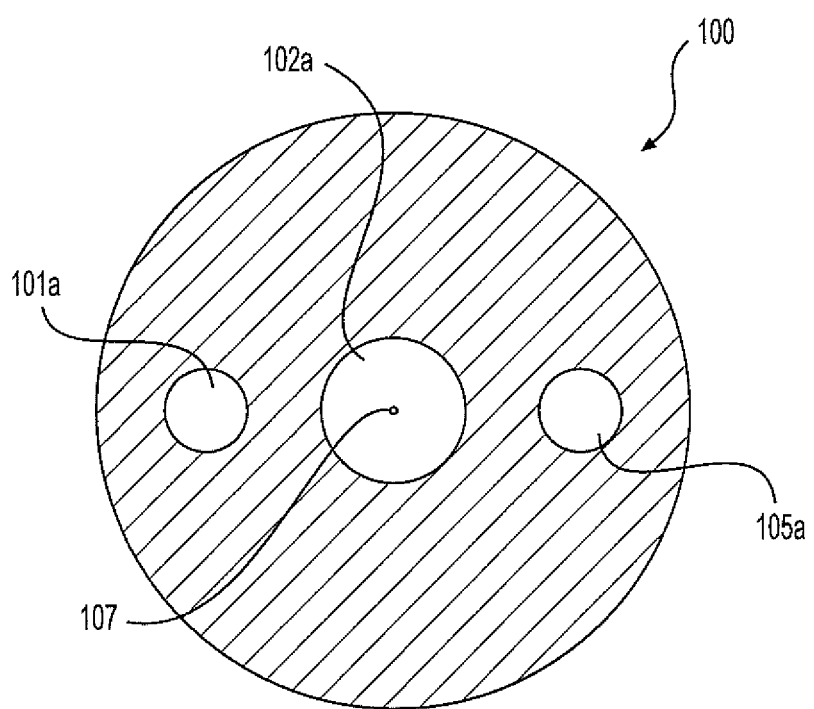
FIG. 1B is a cross-sectional view taken along lines 1B-1B of FIG. 1A.

FIG. 1B shows the cross-sectional view taken along the 1B-1B plane of the catheter 100 of FIG. 1A. The catheter 100 is illustrated in section in FIG. 1B along with relative positions of the lumens 101a, 102a and 105a, for example. Also, FIG. 1B illustrates a relative position of the radioactive wire 107 within the lumen 102a. The central lumen 102a allows for selectively inserting and positioning the radioactive wire, such as the radioactive wire 107, a radioactive seed or other suitable treatment medium, for delivery of the medical treatment, for example.

Figure 1C:
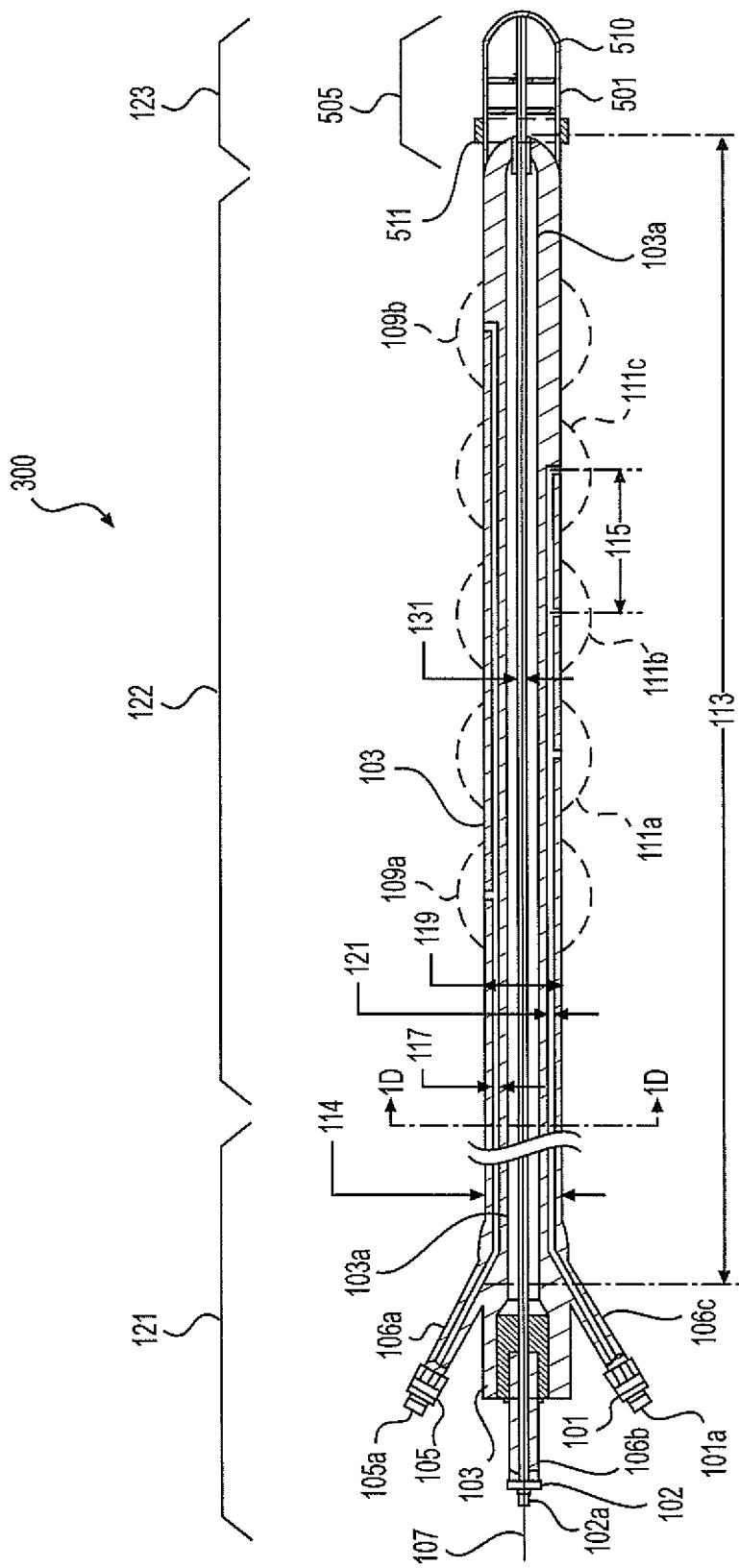
FIG. 1C is a plan view of an embodiment of a multi-purpose balloon catheter according to the present invention having an embodiment of an applicator extender in association with the distal position of the catheter.

Referring to FIG. 1C, another embodiment of a multi-purpose balloon single intra-cavity catheter 300 is illustrated. The catheter 300 is similar to the catheter 100 of FIG. 1A, as described, including the balloons 109a, 109b, 111a, 111b, 111c, and the corresponding lumens 101a, 102a and 105a with the connectors or locking mechanisms 101, 102 and 105, as described, and can be of suitable shapes, dimensions and materials, as described in relation to the catheter 100. However, the catheter 300 also includes an embodiment of an applicator extender 505 communicatively associated with the non-branching distal end portion 123 of the catheter 300, the applicator extender 505 being configured to be in communication with the central portion 122 of the catheter 300 for delivering the medical treatment. The applicator extender 505 includes a lower portion or a lower chamber 507 and an upper portion or an upper chamber 509 for delivering a radiation dose, such as to the esophagus, such as through the radioactive wire 107, for example.

A secondary treatment radiation balloon wire can be inserted into the applicator extender 505 through the middle section having a membrane that can be made of silicone, to deliver a treatment fluid or treatment medium, for example. The applicator extender 505 can be associated with or include a suitable connector or fastening mechanism 511, such as a suitable luer lock, to allow fitting the applicator extender 505 with the catheter 300 in association with the non-branching distal end portion 123 of the catheter 300 end, such as in FIG. 1C, for example. The applicator extender 505 in conjunction with an embodiment of a treatment balloon is illustrated in greater detail and further described herein in relation to FIGS. 1F, 1G and 1H.

Figure 1D:
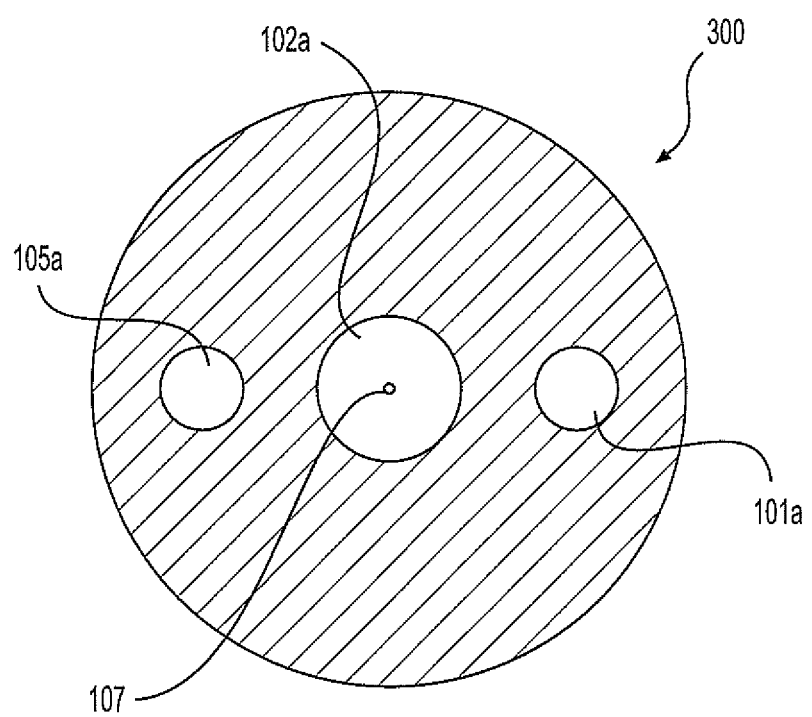
FIG. 1D is a cross-sectional view taken along lines 1D-1D of the embodiment of the catheter of FIG. 1C.

FIG. 1D illustrates is a cross-sectional planar view taken along the 1D-1D plane of the catheter 300 of FIG. 1C. The catheter 300 is illustrated in section in FIG. 1D along with relative positions of the lumens 101a, 102a and 105a, for example. Also, FIG. 1D illustrates a relative position of the radioactive wire 107 within the lumen 102a. The central lumen 102a allows for selectively inserting and positioning the radioactive wire, such as the radioactive wire 107, or other suitable treatment medium, for delivery of the medical treatment, for example.

Figure 1E:
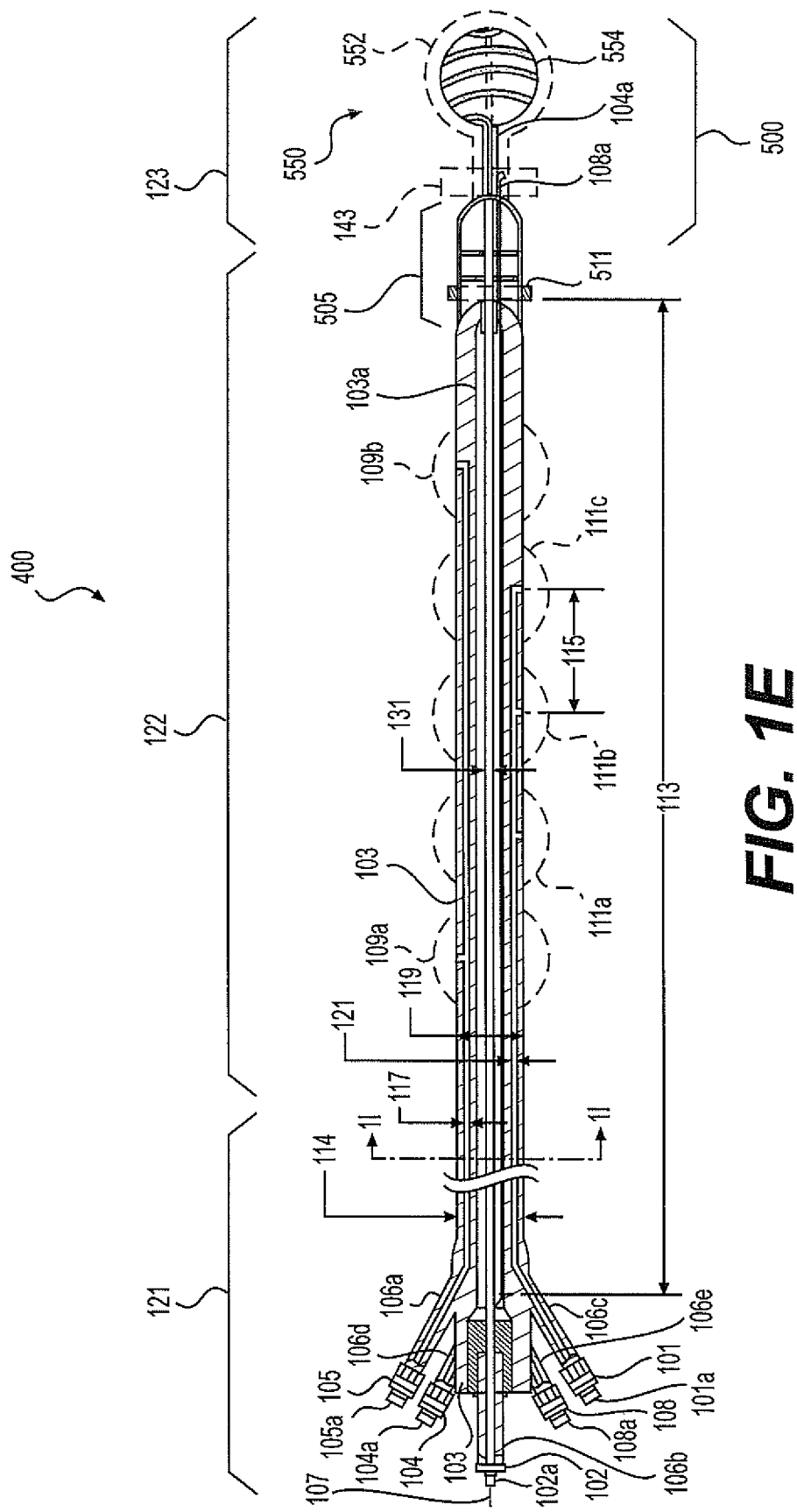
FIG. 1E is a plan view of an embodiment of a multi-purpose balloon catheter according to the present invention having a treatment balloon configuration and an embodiment of an applicator extender in conjunction with an embodiment of a treatment balloon.

Referring to FIG. 1E, another embodiment of a multi-purpose balloon single intra-cavity catheter 400 is illustrated. The catheter 400 is similar to the catheter 100 of FIG. 1A and the catheter 300 of FIG. 1C, as described, including the balloons 109a, 109b, 111a, 111b, 111c, and the corresponding lumens 101a, 102a and 105a with the connectors or locking mechanisms 101, 102 and 105, as described, and can be of suitable shapes, dimensions and materials, as described in relation to the catheters 100 and 300. However, the catheter 400 also includes an embodiment of an applicator extender balloon assembly 500 at the non-branching distal end portion 123 of the catheter 400 that includes the applicator extender 505, such as also illustrated in FIG. 1C, and an embodiment of a secondary treatment balloon 550.

The applicator extender 505 provides a connection with the lumen 102a for delivery of a radiation dose, or for delivery of a therapeutic agent, to the secondary treatment balloon 550 for the medical treatment, such as to a cavity formed by or in the stomach or a surgically created cavity, such as through the radioactive wire 107, for example. A secondary treatment radiation balloon wire, such as the radioactive wire 107, can be inserted into the lumen 102a and through the applicator extender 505 through the middle section having a membrane that can be made of silicone, and can also deliver a treatment fluid or treatment medium, for example, to the secondary treatment balloon 550.

The secondary treatment balloon 550 includes an outer secondary treatment balloon 552 and an inner secondary treatment balloon 554. The outer secondary treatment balloon 552 and the inner secondary treatment balloon 554 can be selectively inflated or deflated to be positioned in a body cavity or a surgically created cavity to be treated and the inner secondary treatment balloon 554 is associated with at least one secondary treatment lumen communicatively connected with the lumen 102a for delivery and removal of a radiation dose, a therapeutic agent or other medical treatment, to be further described in relation to FIGS. 1F, 1G and 1H.

Additionally, the catheter 400 includes neck portions 106d and 106e and corresponding lumens 104a and 108a that are desirably associated with a corresponding suitable connector or connecting mechanism 104 and 108, such as suitable luer locks 104 and 108, which can be a male or a female connection, for example. The lumens 104a and 108a can be extended through the applicator extender 505, such as by a suitable connector lumen in the applicator extender 505, to be placed in communication with the secondary treatment balloon 550. The lumen 104a is communicatively positioned in association with the inner secondary treatment balloon 554 and the lumen 108a is communicatively positioned in association with the outer secondary treatment balloon 552 to respectively selectively inflate or deflate the inner secondary treatment balloon 554 and the outer secondary treatment balloon 552 to position and stabilize the secondary treatment balloon 550 in a body cavity to be treated.

Similarly, the lumens 104a and 108a associated with the luer locks 104 and 108, respectively, can receive and remove a fluid medium, such as saline solution or a gaseous medium, such as by a syringe or other suitable delivery mechanism or machine, such as a pump, to selectively inflate or deflate the inner secondary treatment balloon 554 and the outer secondary treatment balloon 552, to provide a corresponding balloon, shape, size and configuration in the body cavity for the treatment, for example.

Additionally, the applicator extender 505 can be associated with or include a suitable connector or fastening mechanism 511, such as a suitable luer lock, to allow fitting with the catheter 400 in association with the non-branching distal end portion 123 of the catheter 400, such as in FIG. 1E, for example. The applicator extender 505 and the secondary treatment balloon 550 can be associated with a further connector or locking mechanism 143, such as a luer lock, to allow selective fitting of the applicator extender 505 with the secondary treatment balloon 550 to allow for secondary treatment balloons 550 of different sizes, shapes and configurations to be communicatively connected with the applicator extender 505 for delivery of the medical treatment, for example.

Also, the applicator extender 505 and the secondary treatment balloon 550, as well as the applicator extender balloon assembly 500, can be integrally formed together with each other and with the catheter 400, or can also suitably be joined together by other suitable processes and methods, such as with a suitable adhesive, glue or tape in addition to the locking mechanism or connector, such as the luer locks 511 and 143, for example. The applicator extender balloon assembly 500 including the applicator extender 505 and various exemplary embodiments of the secondary treatment balloon 550 are illustrated in greater detail and further described herein in relation to FIGS. 1F, 1G and 1H.

Figure 1F:
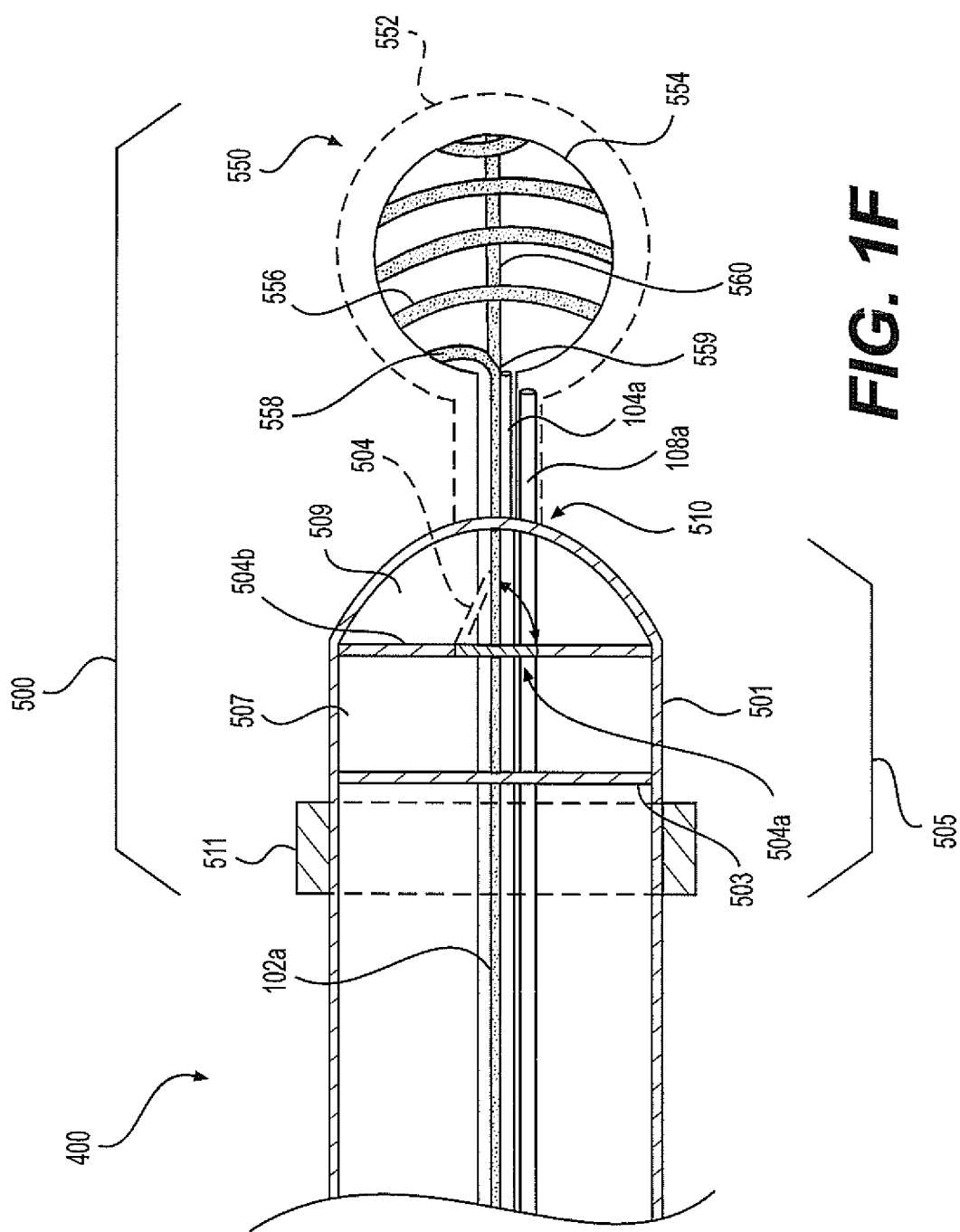
FIG. 1F is an embodiment of an applicator extender in conjunction with an embodiment of a treatment balloon that can be fitted in association with the distal end portion of the embodiment of the catheter of FIG. 1E, or that can be fitted in association with the distal end portion of the embodiment of the catheter of FIG. 1A.

Referring now to FIG. 1F, there is illustrated the catheter 400 with an embodiment of the applicator extender balloon assembly 500 that includes an embodiment of the applicator extender 505 and an embodiment of the secondary treatment balloon 550 associated with the catheter 400 and with the various lumens of FIG. 1E, in greater detail. In the embodiment of the applicator extender balloon assembly 500 of FIG. 1F, the applicator extender 505 and the secondary treatment balloon 550 are integrally formed or are joined together with each other at 510, such as by being suitably joined together by suitable processes and methods, such as with a suitable adhesive, glue or tape, for example. In the embodiment of applicator extender balloon assembly 500, the applicator extender 505 can be suitably joined to the catheter 400 by a suitable locking mechanism or connector, such as the luer lock 511, or can be integrally formed or are joined together with the catheter 400, such as by being suitably joined together by suitable processes and methods, such as with a suitable adhesive, glue or tape, for example.

The applicator extender 505 in FIG. 1F, also includes a lower or proximal chamber 507 and a distal or upper chamber 509 that can receive a radioactive or other therapeutic medium or a contrast medium, such as through the central lumen 102a, for example. The applicator extender 505 can include a base 503, having a suitable membrane or being made from a suitable material to allow passage of one or more lumens, and an outer wall 501 that can form respective portions of the lower chamber 507 and the upper chamber 509 and that can be communicatively connected to the connector or locking mechanism 511 or that can be otherwise communicatively connected to the catheter 400, as described. The lower chamber 507 and the upper chamber 509 each can selectively include a suitable fluid medium or a treatment agent, such as a radioactive fluid or a contrast agent, that can be used for mapping a position or for the medical treatment and can be selectively introduced though the central lumen 102a, for example.

The applicator extender 505 also includes an aperture 504a that can be selectively opened or closed by a gate member 504 that can be either adapted to be perforated or that can be adapted to be selectively opened or closed by passage or removal of the central lumen 102a or of an extension thereof in the applicator extender 505, as described, and/or by the lumens 104a and 108a or an extension thereof in the applicator extender 505, as described. The gate member 504 can be formed in or as a part of a separation wall 504b, formed between the lower chamber 507 and the upper chamber 509, and can be made from silicone, a rubber type material, or other suitable material, or can be a membrane of a suitable material, for example.

The applicator extender 505 also includes an aperture 504a that can be selectively opened or closed by a gate member 504 that can be either adapted to be perforated or that can be adapted to be selectively opened or closed by passage or removal of the central lumen 102a or of an extension thereof in the applicator extender 505, as described, and/or by the lumens 104a and 108a or an extension thereof in the applicator extender 505, as described. The gate member 504 can be formed in or as a part of a separation wall 504b, formed between the lower chamber 507 and the upper chamber 509, as can be formed of silicone or a rubber type material, or other suitable material, or can be a membrane of a suitable material, for example.

As described in relation to FIG. 1E, the lumens 104a and 108a can be extended through the applicator extender 505, such as by a suitable connector lumen in the applicator extender 505, to be placed in communication with the secondary treatment balloon 550. The lumen 104a is in communication with the inner secondary treatment balloon 554 and the lumen 108a is in communication with the outer secondary treatment balloon 552 to respectively selectively inflate or deflate the inner secondary treatment balloon 554 and the outer secondary treatment balloon 552 to position and/or stabilize the secondary treatment balloon 550, the outer secondary treatment balloon 552 and/or the inner secondary treatment balloon 554, in a body cavity to be treated.

Similarly, the lumens 104a and 108a can receive and remove a fluid medium, as previously described, such as saline solution or a gaseous medium, such as by a syringe or other suitable delivery mechanism, such as a pump, to selectively inflate or deflate the inner secondary treatment balloon 554 and the outer secondary treatment balloon 552, to provide a corresponding balloon, shape, size and configuration in the body cavity for the treatment, for example.

The inner secondary treatment balloon 554 has at least one or both of a first secondary treatment lumen 556 and a second secondary treatment lumen 560. The first secondary treatment lumen 556 can be positioned in association with the periphery of the inner secondary treatment balloon 554 and can be integrally formed with or affixed to or otherwise positioned in conjunction with the inner secondary treatment balloon 554, such as by a suitable glue or adhesive, for example. The first secondary treatment lumen 556 can be positioned in association with the periphery of the inner secondary treatment balloon 554, such as either in association with an interior surface or in association with an exterior surface of the inner secondary treatment balloon 554, desirably in a generally spiral type configuration, such as illustrated in FIG. 1F, for example. The first secondary treatment lumen 556 is communicatively connected to the central lumen 102a or an extension thereof in the applicator extender balloon assembly 500 by a connector or connector portion 558 to deliver a radioactive dose or other medical treatment through the central lumen 102a to a treatment site in a cavity, such as by insertion of the radioactive wire 107 or providing a therapeutic agent through the central lumen 102a, the connector 558 and the first secondary treatment lumen 556, for example.

In the inner secondary treatment balloon 554, the second secondary treatment lumen 560 can be integrally formed with or affixed to or otherwise positioned in conjunction with the inner secondary treatment balloon 554, such as by a suitable glue or adhesive, for example. The second secondary treatment lumen 560 is communicatively connected to the central lumen 102a by a connector or connector portion 559 to deliver a radioactive dose or other medical treatment through the central lumen 102a to a treatment site in a cavity, such as by insertion of the radioactive wire 107 or providing a therapeutic agent through the central lumen 102a, the connector 559 and the second secondary treatment lumen 560, for example. The second secondary treatment lumen 560 is desirably formed in an interior portion of the inner secondary treatment balloon 554 desirably extending in a generally longitudinal direction in a generally central portion of the inner secondary treatment balloon 554, for example.

Referring now to FIG. 1G, there is illustrated the catheter 400 with an embodiment of the applicator extender balloon assembly 500 that includes an embodiment of the applicator extender 505 and an embodiment of the secondary treatment balloon 550 associated with the catheter 400 and with the various lumens of FIG. 1E, in greater detail. The applicator extender balloon assembly 500 in association with the catheter 400 in FIG. 1G has similar components and structure to that described with respect to the applicator extender balloon assembly 500 illustrated in FIG. 1F. However, in the applicator extender balloon assembly 500 of FIG. 1G, there is included a connector or locking mechanism 143, such as a suitable luer lock, that can include suitable male or female connectors 143a and 143b to connect the applicator extender 505 and the secondary treatment balloon 550 for a treatment. Also, in the applicator extender balloon assembly 500 of FIG. 1G the inner secondary treatment balloon 554 can only include, for example, the second secondary treatment lumen 560 and the connector 559, with the first secondary treatment lumen 556 being optionally indicated by the dashed lines and the connector 558 (illustrated in FIG. 1F) not being shown in FIG. 1G.

Referring now to FIG. 1H, there is illustrated the catheter 400 with an embodiment of the applicator extender balloon assembly 500 that includes an embodiment of the applicator extender 505 and an embodiment of the secondary treatment balloon 550 associated with the catheter 400 and with the various lumens of FIG. 1E, in greater detail. The applicator extender balloon assembly 500 in association with the catheter 400 in FIG. 1H has similar components and structure to that described with respect to the applicator extender balloon assembly 500 illustrated in FIG. 1F. However, in the applicator extender balloon assembly 500 of FIG. 1H, there is included a connector or locking mechanism 143, such as a suitable luer lock, that can include suitable male or female connectors 143a and 143b to connect the applicator extender 505 and the secondary treatment balloon 550 for a treatment. Also, in the applicator extender balloon assembly 500 of FIG. 1H the inner secondary treatment balloon 554 can only include, for example, the first secondary treatment lumen 556 and the connector 558, with the second secondary treatment lumen 560 and the connector 559 being optionally indicated by the dashed lines.

Figure 1I:
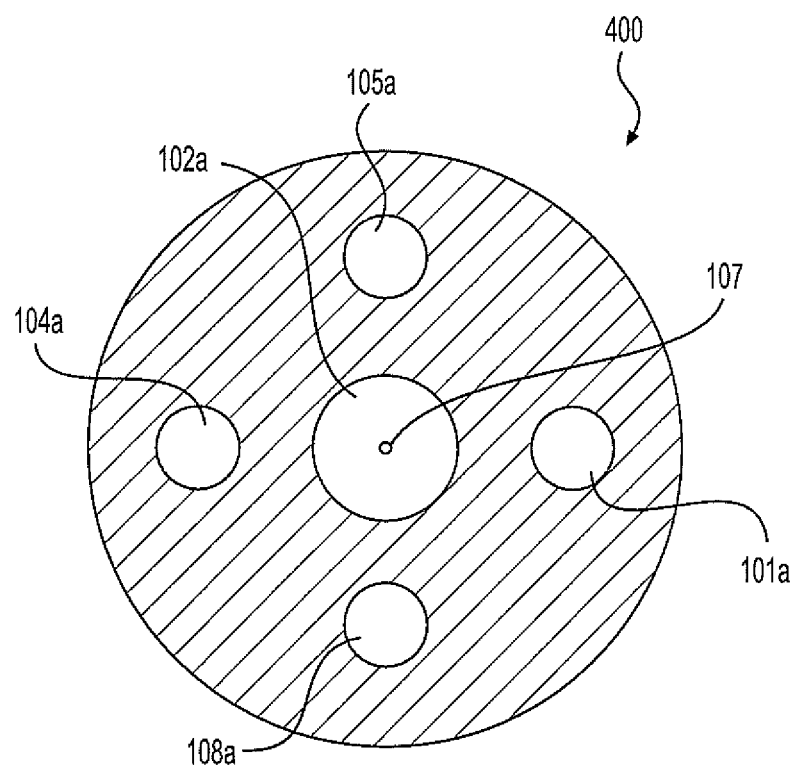
FIG. 1I is a cross-sectional view taken along lines 1I-1I of the embodiment of the catheter of FIG. 1E.

Referring to FIG. 1I, there is illustrated a cross-sectional planar view taken along the 1I-1I plane of the catheter 400 of FIG. 1E. The catheter 400 is illustrated in section in FIG. 1I along with relative positions of the lumens 101a, 102a, 104a, 105a and 108a, for example. Also, FIG. 1I illustrates a relative position of the radioactive wire 107 within the lumen 102a. The central lumen 102a allows for selectively inserting and positioning the radioactive wire, such as the radioactive wire 107, or other suitable treatment medium, for the delivery of the medical treatment, for example.

The catheters 100, 300 and 400, and the various balloons and components thereof including the applicator extender balloon assembly 500 and components thereof can be made of various suitable materials, including, for example, nylon, polyurethane, Polyether block amide Pebax®, poly(ethylene terephthalate), commonly abbreviated PET or other thermoplastic elastomers. Nylon can be desirably used, since it can be fused together with the catheter, for example.

Figure 2A:
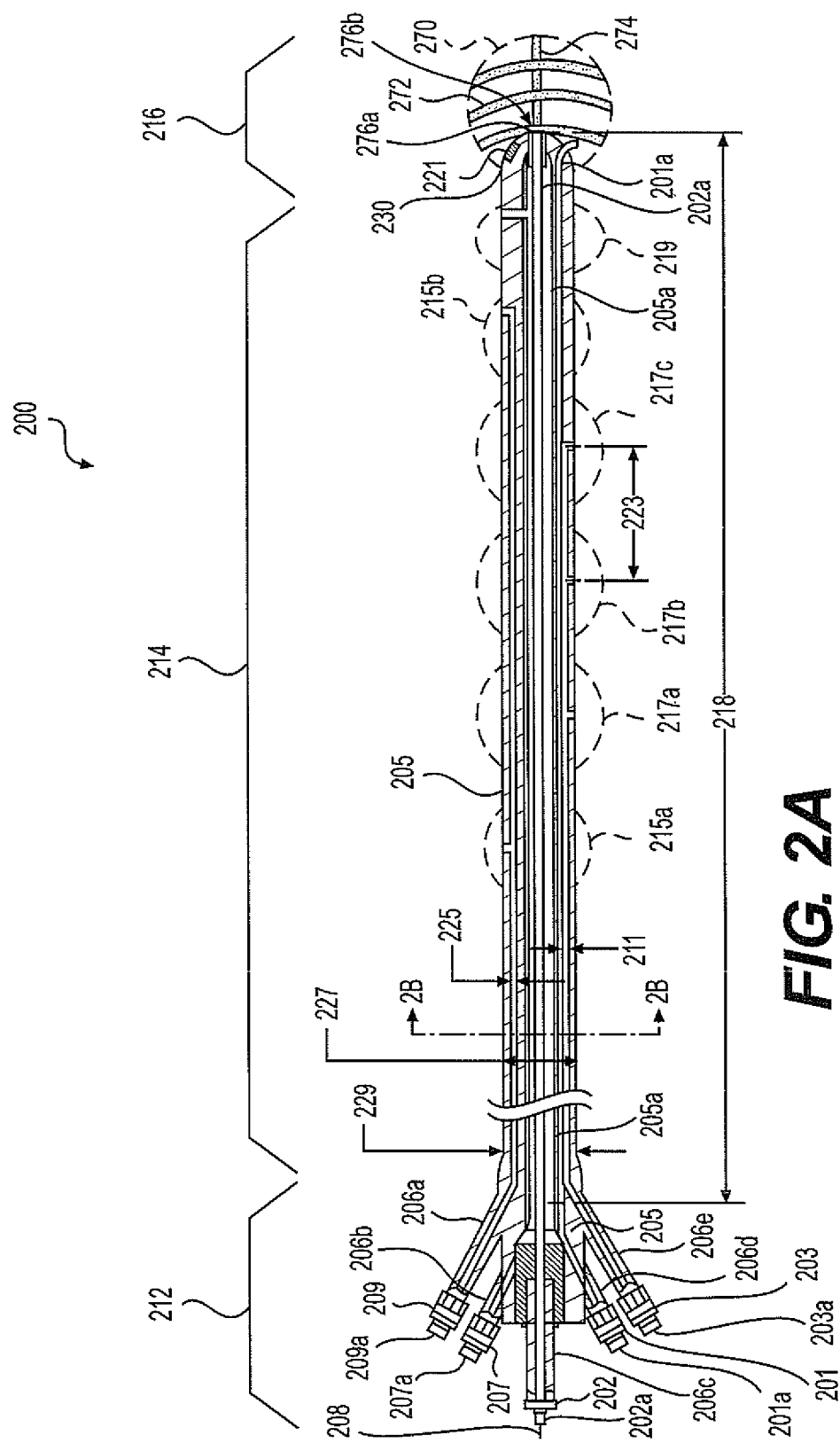
FIG. 2A is a longitudinal plan view of an embodiment of a multi-purpose balloon catheter according to the present invention.

Referring now to FIG. 2A, there is provided a multipurpose balloon single intra-cavity catheter 200 having a plurality of various sized balloons that may be arranged in a plurality of independent and distinct balloons groups, and can enable fixing, stabilizing or positioning of radioactive material, such as radioactive wires, in a cavity, such as in the esophagus or in other organs or in bodily or surgically created cavities, to deliver a radiation dose or other therapeutic agent to a targeted portion of a body for the medical treatment. Moreover, the catheter 200 can allow for diagnosing the anatomy of abnormal organ shape by evaluating the balloon shape (with contrast agent) by comparing to shapes of normal healthy patient organs, for example.

FIG. 2A shows an embodiment of the catheter 200, similar to the structure of the catheter 100 of FIG. 1A fitted with a secondary treatment balloon 270 as shown in FIG. 2A that is adapted to receive a radioactive wire that encircles or is arranged in association with an inner portion of the balloon for delivering a relatively higher dose of radiation and to position the balloon in the cavity or organ for treatment. The balloon attached to the catheter 200 can include outer and inner balloons to position and deliver the medical treatment. The outer balloon can also assist in protecting the inner balloon that is adapted to receive the radioactive material, such as radioactive wire, or a therapeutic agent for the medical treatment, as to be further described.

Referring now to the drawings in greater detail, there is illustrated in FIG. 2A an embodiment of the multi-purpose balloon single intra-cavity catheter 200 according to the teachings of the invention. The multi-purpose balloon single intra-cavity catheter 200 includes a proximal end portion 212, a central portion 214 having, for example, a generally tubular shaped body 205, and a non-branching distal end portion 216, with the non-branching distal end portion 216 including a suitable marker such as an X-ray marker 221, to indicate a position of the non-branching distal end portion 216 of the catheter 200. The X-ray marker 221 typically can be gold, lead, tungsten or other heavy metal suitable for X-ray visualization, or can be other suitable material, depending on the use or application, and should not be construed in a limiting sense.

The multi-purpose balloon single intra-cavity catheter 200 can be made of various suitable materials, such as a polymeric material, such as polyurethane or polyacrylic, among other examples, depending on the use or application, for example. Typically, a length 218 of the multi-purpose balloon single intra-cavity catheter 200 of FIG. 2A is about 78 cm to the tip area from the base area of the multi-purpose balloon single intra-cavity catheter 200, but the catheter 200 can be of various suitable lengths and dimensions, depending on the use or application, for example. A diameter 229 of the central portion 214 of the catheter 200 of FIG. 2A is typically 0.45 cm, but can be of various suitable diameters, depending on the use or application, for example.

The proximal end portion 212 of the catheter 200 includes the plurality of neck portions 206a, 206b, 206c, 206d and 206e, made of similar suitable material as the catheter 200. The neck portions 206a, 206b, 206c, 206d and 206e each include a corresponding lumen 201a, 202a, 203a, 207a and 209a therein that extends from the proximal end portion 212, such as within the catheter 200, for balloon inflation or for the delivery of the medical treatment, for example. The neck portions 206a, 206b, 206c, 206d and 206e and corresponding lumens 201a, 202a, 203a, 207a and 209a are desirably associated with a corresponding suitable connector or connecting mechanism 201, 202, 203, 207 and 209, such as suitable luer locks 201, 202, 203, 207 and 209, that can be a male or a female connection, for example.

For example, the luer-locks 203, 207 and 209 can be fitted with syringes for selectively inflating balloons 215a, 215b, balloons 217a, 217b, and 217c and balloon 219 to a predetermined size, for a particular use or application, for example. The balloons 215a, 215b, the balloons 217a, 217b, and 217c and the balloon 219 being desirably located in association with the central portion 214 to facilitate positioning and/or stabilizing the catheter 200 for delivery of a treatment. In the catheter 200, the lumen 203a associated with the luer lock 203 can receive and remove a fluid medium, such as saline solution or a gaseous medium, such as by a syringe or other suitable delivery mechanism, such as a pump, to selectively inflate or deflate the balloons 217a, 217b, and 217c, for example.

Also, the lumen 207a associated with the luer lock 207 can receive and remove a fluid medium, such as saline solution or a gaseous medium, such as by a syringe or other suitable delivery mechanism, such as a pump, to selectively inflate or deflate the balloon 219, for example. Similarly, the lumen 209a associated with the luer lock 209 can receive and remove a fluid medium, such as saline solution or a gaseous medium, such as by a syringe or other suitable delivery mechanism, such as a pump, to selectively inflate or deflate the balloons 215a and 215b, for example. The locking mechanism or connector, such as provided by the luer locks 203, 207 and 209, when affixed to the catheter 200 can provide for selectively not allowing or selectively allowing a fluid medium, such as including fluids, fluid or gaseous mediums, or air, or allowing a contrast medium, for example, to pass through a corresponding connecting point provided by the connector or connecting mechanism 203, 207 and 209, such as luer locks, with the catheter 200. As illustrated in FIG. 2A, the balloons 215a, 215b, 217a, 217b, 217c and 219 can be arranged in a plurality of independent and distinct balloon groups in association with the central portion 214 of the catheter 200. For example, as illustrated from FIG. 2A, the balloons 215a and 215b can form a first independent and distinct balloon group, the balloons 217a, 217b and 217c can form a second independent and distinct balloon group, and the balloon 219 can form a third independent and distinct balloon group. Each independent and distinct balloon group can be selectively inflated or deflated or can also receive or have removed a contrast liquid or other contrast medium independently of the balloons of another independent and distinct balloon group, such as through corresponding ones of the plurality of connectors, such as connectors 203, 207 and 209, and through the associated corresponding ones of the plurality of the lumens, such as lumens 203a, 207a and 209a, for example.

As depicted in FIG. 2A, the central lumen 202a associated with the connector 202, such as a luer lock, can be used to insert a radioactive wire 208 or a radioactive seed, for example, as a radiation source for treatment at a specific or predetermined site or location of or within the organ or other cavity, into the catheter 200. Also, the central lumen 202a associated with the locking mechanism or connector 202, such as a luer lock, can be used with suction or a syringe to remove bodily fluids or material from a cavity in a body using the treatment catheter 200, for example. The central lumen 202a can be positioned in a larger main lumen 205a extending through the catheter 200, as illustrated in FIG. 2A. The locking mechanism or connector 202 for the central lumen 202a can allow medical personnel to have a relatively easier controlled delivery and guidance for the delivery of the medical treatment or extraction within a treatment area, for example.

Selectively inflating the balloons 215a, 215b, 217a, 217b, 217c and 219 can allow for selectively positioning and stabilizing the catheter 200 for administration of the medical treatment or for removal of bodily fluids or material in or within a cavity, such as in a bodily organ or in a cavity region, such as in or within the esophagus, rectum, stomach or a surgically created cavity, such as in or within the breast, another organ or bodily tissue, such as through the lumen 202a, for example. The lumens 203a, 207a and 209a and the inflated balloons 215a, 215b, 217a, 217b, 217c and 219 can contain a contrast liquid or other contrast medium, for contrast purposes in imaging applications. The lumens 203a, 207a and 209a can also be used for inflation or deflation of the balloons 215a, 215b, 217a, 217b, 217c and 219, for positioning, stabilization and/or treatment, for example.

As discussed herein, the catheter 200 includes a plurality of balloons, such as the balloons 215a, 215b, 217a, 217b, 217c and 219, arranged in a plurality of independent and distinct balloon groups, such as the first balloon group including balloons 215a and 215b, the second balloon group including balloons 217a, 217b, 217c, and the third balloon group including balloon 219. The lumens of the catheter 200, such as the lumens 203a, 207a and 209a, can be communicatively connected to a single or to any of various pluralities of balloons. For example, the lumen 203a can be connected with balloons 217a, 217b, 217c of the second balloon group, the lumen 207a can be connected to the balloon 219 of the third balloon group, and the lumen 209a can be connected to balloons 215a and 215b of the first balloon group, as illustrated in FIG. 2A, for example. Also, the catheter 200 can have any of various other suitable connection arrangements with more or less lumens or balloons, depending on the use or application, for example.

Further, the balloons, such as the balloons 215a, 215b, 217a, 217b, 217c and 219, can have any of various suitable sizes or shapes, such as cylindrical, spherical, oval, oblong, toroidal, or other suitable shapes, depending on the use or application, for example. In the catheter 200, the first independent and distinct balloon group including balloons 215a and 215b, the second independent and distinct balloon group including balloons 217a, 217b and 217c, and the third independent and distinct balloon group including balloon 219 each can be of a different size or shape from the balloons of the other groups, for example, and can assist in positioning and stabilizing the catheter 200 in a cavity, such as an organ, a body cavity or a surgically created cavity, for the delivery of the medical treatment.

The lumens, such as the lumens 201a, 202a, 203a, 207a and 209a, can have any of various suitable sizes, shapes or configurations, such as cylindrical, rectangular, oval, or other suitable shapes or configurations, depending on the use or application, for example. Also, a typical dimension of a diameter of the lumens, such as indicated at 211 for diameter of the lumen 203a and as indicated at 225 for a diameter of the lumen 209a, for inflating the corresponding balloons 215a, 215b, 217a, 217b, 217c and 219 can be typically in a range of from about 0.8 mm to about 1.5 mm, for example, but can be of various suitable dimensions, depending on the use or application, and should not be construed in a limiting sense.

Further, the spacing between each of the centers of adjacent ones of the balloons 217a, 217b and 217c can, for example, correspond to the spacing between adjacent exit points of the lumen 203a, can be a same or a different spacing, depending on the use or application, such as desirably being spaced apart by about 2.5 cm from each other as indicated at 223, for example. Also, the spacing between each of adjacent balloons of the catheter 200, such as the balloons 215a, 215b, 217a, 217b, 217c and 219, can be same or different for each pair of adjacent balloons of the catheter 200, depending on the use or application, for example. The first balloon group including the balloons 215a and 215b, the second balloon group including the balloons 217a, 217b and 217c, and the third balloon group including the balloon 219 are each independently arranged from each other balloon group on the catheter 200 along the length 218 of the catheter 200, as illustrated in FIG. 2A. Also, the lumens, such as the lumens 201a, 202a, 203a, 207a and 209a, can be positioned within the interior of the catheter 200, such interior of the catheter 200 being indicated by the numeral 227, or can be positioned or integrally formed on or in an exterior surface or layer of the catheter 200, for example, depending on the use or application, for example.

The balloons, such as the balloons 215a, 215b, 217a, 217b, 217c and 219 can be made of nylon, polyurethane, Polyether block amide Pebax®, poly(ethylene terephthalate) commonly abbreviated PET, or other thermoplastic elastomers or other suitable materials, depending on the use or application, for example. Additionally, one or more of the balloons 215a, 215b, 217a, 217b, 217c and 219 and all of, part of or a portion of the catheter 200, such as including the body 205 of the central portion 214 of the catheter 200, can be coated or impregnated with various suitable coatings for ease of assembly such as a silicone type coating, or the balloons, such as the balloons 215a, 215b, 217a, 217b, 217c and 219, and/or the catheter, such as the catheter 200, can be impregnated or coated with various suitable therapeutic or medicinal agents for treatment at a site within the body, such as by elution of the agent from the balloon or the catheter, for example.

In an embodiment, all of, a part of or a portion of the catheter 200, as well as one or more of the balloons associated with the catheter 200, such as the balloons 215a, 215b, 217a, 217b, 217c and 219, can be uncoated or can be coated with a lubricant for lubrication for ease of positioning the catheter 200 at a treatment site, or can be coated or formed with antimicrobial or medicinal agents for the delivery of the medical treatment at the treatment site, for example. In this regard, in various embodiments of catheters, such as the catheter 200, various therapeutic drugs or agents can be coated onto the surface of one or more of the balloons, such as the balloons 215a, 215b, 217a, 217b, 217c and 219, or coated onto the surface of all of, part of or a portion of the catheter, such as the catheter 200, for releasing the therapeutic drug or agent internally to a specific location of the cavity being treated.

The catheter 200 of FIG. 2A having a plurality of connectors or locking mechanisms 201, 202, 203, 207 and 209, such as the luer-locks as examples of connectors or locking mechanisms, and a plurality of balloons, such as the balloons 215a, 215b, 217a, 217b, 217c and 219, can be inserted into various body cavities, such as the esophagus, but is not limited thereto and can also be inserted for the delivery of the medical treatment into other cavities, such as the rectum, vagina, etc., or surgically created cavities, wherein the radioactive wire, or other radioactive or therapeutic material or other therapeutic agent, can provide the requisite radiation dose or the medical treatment to treat cancerous growth or other medical conditions. Typically, the dimension of the radioactive wire, such as the radioactive wire 208, that can be inserted into the central lumen 202a, is desirably in a range of about 0.5 mm to about 0.8 mm, for example, but can be of various suitable dimensions and configurations depending on the use or application.

Desirably, the radioactive wire, such as the radioactive wire 208, is made of a suitable radioactive material, such as Iridium-192, Cobalt 60 and Yttrium 168, for example. The high dose rate (HDR) treatment delivered through the catheter, such as the catheter 200, can be conducted with Ir-192, Au-198, I-125 and Cs-131, for example. Typically, the dose of radiation delivered by the radioactive wire, such as the radioactive wire 208, is about 1 Curie to about 10 Curies per seed, but can be any suitable dose, depending on the use or application.

Also, HDR afterloaders can be used in conjunction with embodiments of the catheters, such as the catheter 200, for delivery of a radiation dose for the medical treatment, such as Varisource, Gamma Med and BEBIG afterloaders or other suitable afterloaders, for example. For a low dose rate (LDR) application delivered through embodiments of catheters, such as the catheter 200, Sr-90 can be used in conjunction with the radiation wire, such as the radioactive wire 208, as well as Cs-131 and Yb-168 can be used as the radiation source, for example. Typically, the dose of radiation using the LDR configuration is usually one thousand times less than the HDR applications, such LDR dose being in a range of about 1 milli Curie to about 10 milli Curies, for example.

An advantage, among others, of embodiments of catheters, such as the catheter 200, is that it can allow for the delivery of the radiation dose or another therapeutic agent to a specific site or a predetermined location of the organ or body cavity, such as via by the radioactive wire 208 through the central lumen 202*a*. Further, embodiments of catheters, such as the catheter 200, can also allow for, at the same time or at different times, the removal of fluid or bodily material from the treatment site area, such as through the central lumen 202*a* or through a main lumen 205*a* that includes the central lumen 202*a*, as well as provide enhanced stabilization and/or positioning of the catheter for treatment. The selective inflation or deflation of the corresponding balloons, such as the balloons 215*a*, 215*b*, 217*a*, 217*b*, 217*c* and 219, can allow for selectively controlling the size of each balloon independently or in conjunction with one or more other balloons, to selectively adjust the location and positioning of the catheter at the treatment site.

Also, the catheter 200 includes, such as illustrated in FIG. 2A, an embodiment of a secondary treatment balloon 270 at the non-branching distal end portion 216 of the catheter 200. The secondary treatment balloon 270 can be selectively inflated or deflated to be positioned in a body cavity or a surgically created cavity for delivery of a radiation dose or other treatment agent to the surrounding tissue. In the catheter 200, the lumen 201*a* associated with a connector or locking mechanism 201, such as a suitable luer lock, can receive and remove a fluid medium, such as saline solution or a gaseous medium, such as by a syringe or other suitable delivery mechanism, such as a pump, to selectively inflate or deflate the secondary treatment balloon 270, for example.

In the embodiment of the catheter 200, the secondary treatment balloon 270 can be integrally formed with or affixed to or otherwise positioned in conjunction with the catheter 200, such as by a suitable glue or adhesive, for example, as indicated at attachment area 230. The secondary treatment balloon 270 has at least one or both of a first secondary treatment lumen 272 and a second secondary treatment lumen 274. The first secondary treatment lumen 272 can be positioned in association with the periphery of the secondary treatment balloon 270, such as illustrated in FIG. 2A, for example, and can be integrally formed with or affixed to or otherwise positioned in conjunction with the secondary treatment balloon 270, such as by a suitable glue or adhesive, for example.

The first secondary treatment lumen 272 is desirably of a generally spiral type configuration, for example, as illustrated in FIG. 2A. The first secondary treatment lumen 272 can be positioned in association with the periphery of the secondary treatment balloon 270, such as either on an interior surface or on an exterior surface of the secondary treatment balloon 270, for example, but desirably is placed in association with an interior surface or portion thereof. The first secondary treatment lumen 272 is communicatively connected to the central lumen 202*a* by a connector or connector portion 276*a* or can be integrally formed therewith to deliver a radioactive dose or other medical treatment agent through the central lumen 202*a* and through the first secondary treatment lumen 272 to a treatment site in a cavity, such as by insertion of the radioactive wire 208 or providing a therapeutic agent through the central lumen 202*a*, the connector 276*a* and the first secondary treatment lumen 272, for example.

The second secondary treatment lumen 274 is also communicatively connected to the central lumen 202*a* by a connector or connector portion 276*b*, or can be integrally formed therewith to deliver a radioactive dose or other medical treatment agent through the central lumen 202*a* and through the second secondary treatment lumen 274 to a treatment site in a cavity, such as by insertion of the radioactive wire 208 or providing a therapeutic agent through the central lumen 202*a*, the connector 276*b* and the second secondary treatment lumen 274, for example. The second secondary treatment lumen 274 is desirably formed in an interior portion of the secondary treatment balloon 270 desirably extending in a generally longitudinal direction in a generally central portion of the secondary treatment balloon 270, for example.

Figure 2B:
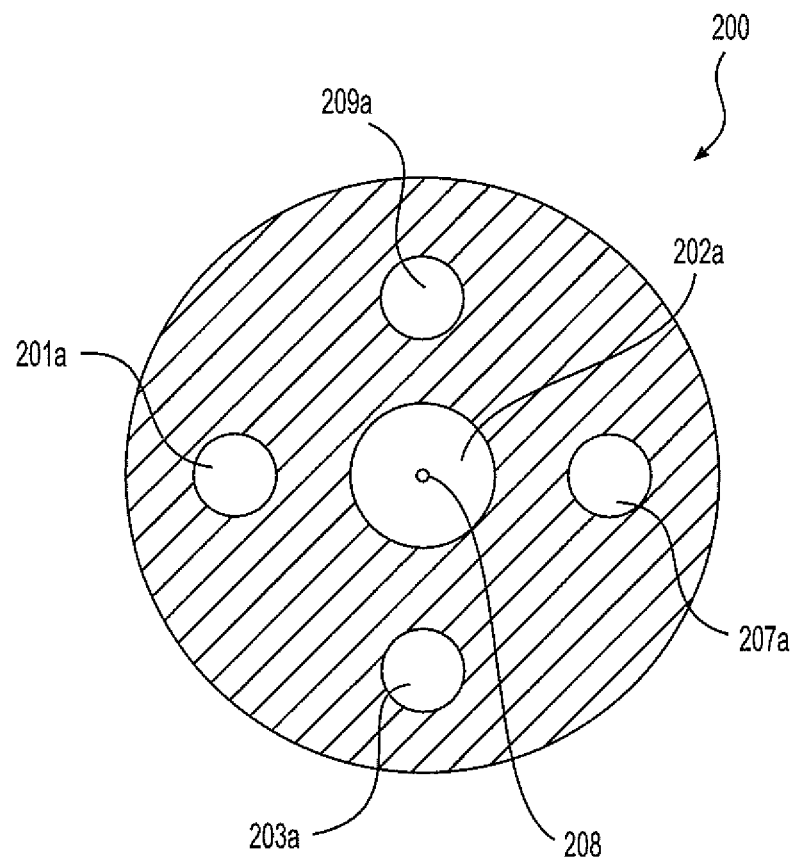
FIG. 2B is a cross-sectional view taken along lines 2B-2B of FIG. 2A.

FIG. 2B shows the cross-sectional view taken along the 2B-2B plane of the catheter 200 of FIG. 2A. The catheter 200 is illustrated in section in FIG. 2B along with relative positions of the lumens 201*a*, 202*a*, 203*a*, 207*a* and 209*a*, for example. Also, FIG. 2B illustrates a relative position of the radioactive wire 208 within the central lumen 202*a*. The central lumen 202*a* allows for selectively inserting and positioning the radioactive wire, such as the radioactive wire 208, or other suitable treatment medium, for delivery of the medical treatment, for example.

Figure 2C:
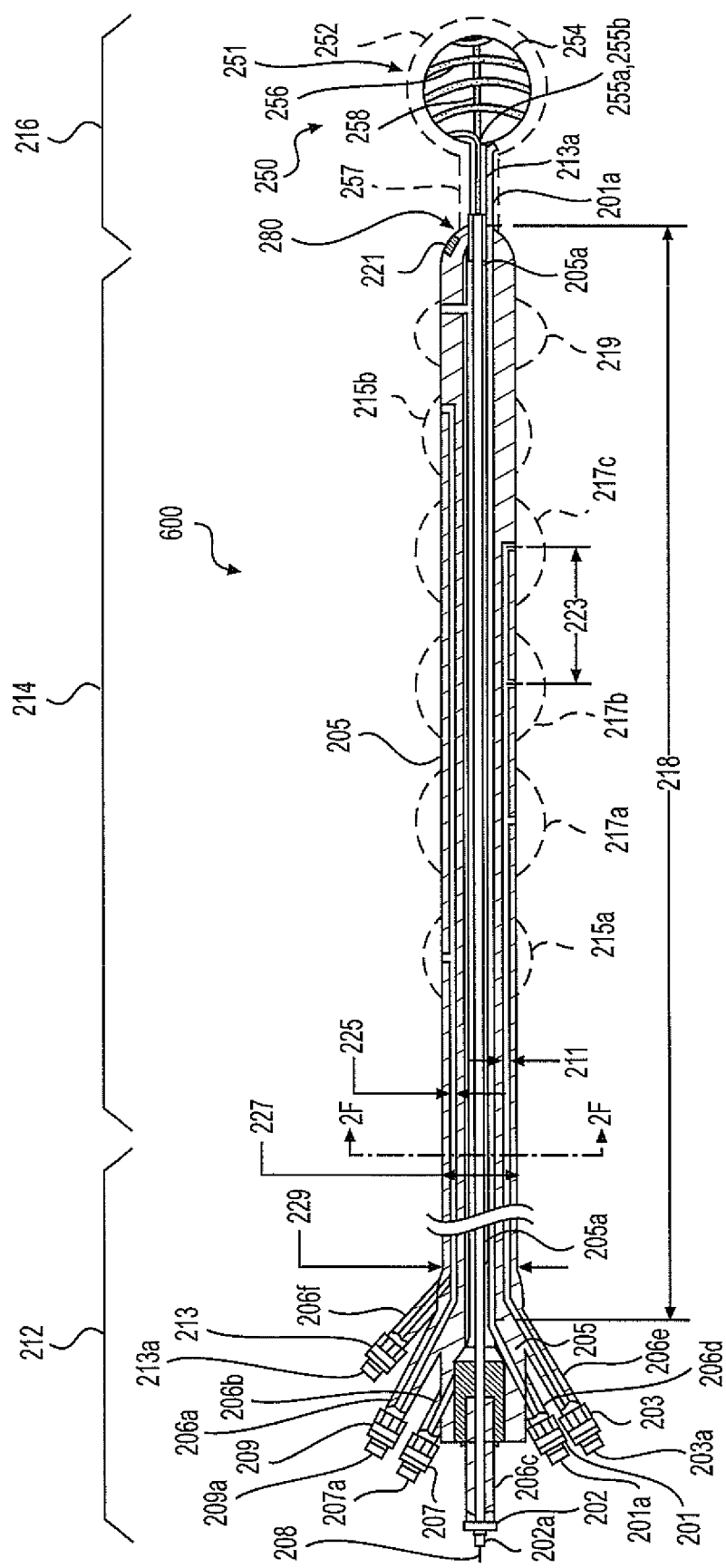
FIG. 2C is a plan view of another embodiment of a multi-purpose balloon catheter fitted with a treatment balloon in association with the distal end portion of the catheter, the treatment balloon having a spiral lumen or a longitudinal lumen adapted to receive a radioactive wire or a radioactive material.

Referring now to FIG. 2C, another embodiment of a catheter 600 is illustrated. The catheter 600 is similar to the catheter 200 of FIG. 2A as to components and structure, as described, including the balloons 215*a*, 215*b*, 217*a*, 217*b*, 217*c* and 219, and the corresponding lumens 201*a*, 202*a*, 203*a*, 207*a* and 209*a* with the connectors or locking mechanisms 201, 202, 203, 207 and 209, as described, and can be of suitable shapes, dimensions and materials, as described in relation to the catheter 200. However, the catheter 600 also includes an additional connector or locking mechanism 213, such as a suitable luer lock, that connects to a neck portion 206*f* of the catheter 600 associated with an additional lumen 213*a*, with the additional lumen 213*a* and the lumen 201*a* associated with an embodiment of a secondary treatment balloon assembly 250 at the non-branching distal end portion 216 of the catheter 600 that is illustrated in greater detail and further described herein in relation to FIGS. 2D and 2E.

Figure 2D:
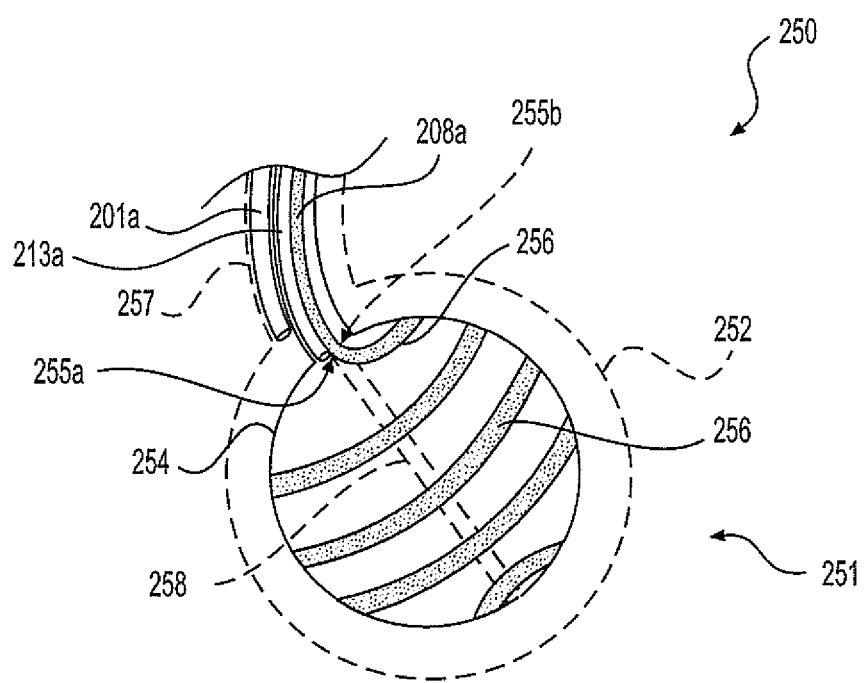
FIG. 2D is an embodiment of a treatment balloon having a spiral lumen or a longitudinal lumen adapted to receive a radioactive wire or a radioactive material as can be with the embodiment of the catheter of FIG. 2C.

Referring to FIGS. 2C and 2D, in the embodiment of the catheter 600, the secondary treatment balloon assembly 250 can be integrally formed with or affixed to or otherwise positioned in conjunction with the catheter 600, such as by a suitable glue or adhesive, for example, as indicated at attachment area 280. The secondary treatment balloon assembly 250 includes a secondary treatment balloon 251 that includes an outer secondary treatment balloon 252 and an inner secondary treatment balloon 254.

The outer secondary treatment balloon 252 and the inner secondary treatment balloon 254 can be selectively inflated or deflated to be positioned in a body cavity or a surgically created cavity to be treated, for example. The lumen 213*a* is in communication with the inner secondary treatment balloon 254 and the lumen 201*a* is in communication with the outer secondary treatment balloon 252 to respectively selectively inflate or deflate the inner secondary treatment balloon 254 and the outer secondary treatment balloon 252 to position and/or stabilize the secondary treatment balloon 251, including the inner secondary treatment balloon 254 and/or the outer secondary treatment balloon 252, in a body cavity or surgically created cavity to be treated. Similarly, the lumens 201a and 213a can receive or can remove a fluid medium, as previously described, such as saline solution or a gaseous medium, such as by a syringe or other suitable delivery mechanism, such as a pump, to selectively inflate or deflate the inner secondary treatment balloon 254 and the outer secondary treatment balloon 252, to provide a corresponding balloon shape, size and configuration in the body cavity for the medical treatment, for example.

The secondary treatment balloon 251 has at least one or both of a first secondary treatment lumen 256 and a second secondary treatment lumen 258, the second secondary treatment lumen 258 being optionally indicated in FIG. 2D. The first secondary treatment lumen 256 can be positioned in association with the periphery of the inner secondary treatment balloon 254 and can be integrally formed with or affixed to or otherwise positioned in conjunction with the inner secondary treatment balloon 254, such as by a suitable glue or adhesive, for example. The first secondary treatment lumen 256 is desirably of a generally spiral type configuration, for example, as illustrated in FIGS. 2C and 2D. The first secondary treatment lumen 256 can be positioned in association with the periphery of the inner secondary treatment balloon 254, such as either on an interior surface or on an exterior surface of the inner secondary treatment balloon 254, for example, but desirably is placed on an interior surface or portion thereof.

The first secondary treatment lumen 256 is communicatively connected to the central lumen 202a by a connector or connector portion 255a, and the central lumen 202a can extend into a neck area 257 of the secondary treatment balloon assembly 250 by a connector portion 208a that can be communicatively connected to or integrally formed with the central lumen 202a, to deliver a radioactive dose or other medical treatment agent through the central lumen 202a, through the connector or connector portion 255a and through the first secondary treatment lumen 256 to a treatment site or a predetermined location in a cavity, such as by insertion of the radioactive wire 208 or providing a therapeutic agent through the central lumen 202a through the neck area 257, the connector 255a and the first secondary treatment lumen 256, for example.

In the inner secondary treatment balloon 254, the second secondary treatment lumen 258 can be integrally formed with or affixed to or otherwise positioned in conjunction with the inner secondary treatment balloon 254, such as by a suitable glue or adhesive, for example. The second secondary treatment lumen 258 is desirably formed in an interior portion of the inner secondary treatment balloon 254 desirably extending in a generally longitudinal direction in a generally central portion of the inner secondary treatment balloon 254, for example.

The second secondary treatment lumen 258 is also communicatively connected to the central lumen 202a by a connector or connector portion 255b, or can be integrally formed therewith to deliver a radioactive dose or other therapeutic agent through the central lumen 202a, the connector 255b and through the second secondary treatment lumen 258 to a treatment site in a cavity, such as by insertion of the radioactive wire 208 or providing a therapeutic agent through the central lumen 202a, the connector 255b and the second secondary treatment lumen 258, for example. The central lumen 202a can extend into the neck area 257 of the secondary treatment balloon assembly 250 by the connector portion 208a that can be communicatively connected to or integrally formed with the central lumen 202a, to deliver a radioactive dose or other medical treatment through the central lumen 202a to a treatment site in a cavity, such as by insertion of the radioactive wire 208 or providing a therapeutic agent through the central lumen 202a through the neck area 257, the connector 255b and the second secondary treatment lumen 258, for example.

Figure 2E:
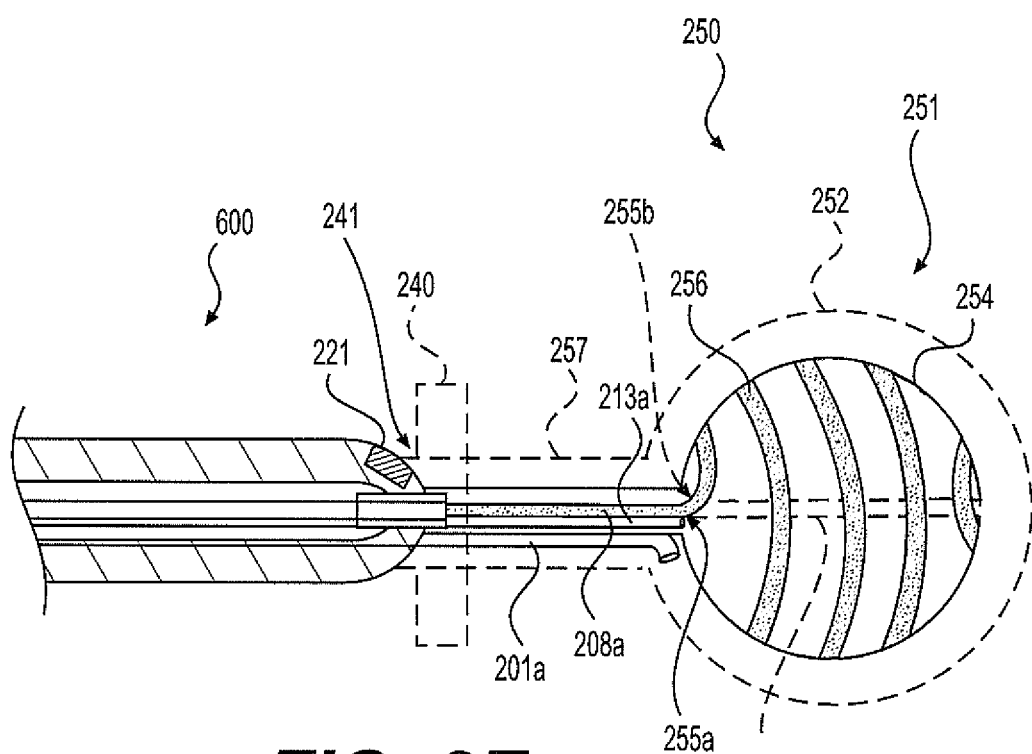
FIG. 2E another embodiment of a treatment balloon having a spiral lumen or a longitudinal lumen adapted to receive a radioactive wire or a radioactive material as can be with the embodiment of the catheter of FIG. 2C.

Referring now to FIG. 2E, there is illustrated the catheter 600 with an embodiment of the secondary treatment balloon assembly 250 that includes similar components and structure to that described with respect to the secondary treatment balloon assembly 250 illustrated in FIGS. 2C and 2D. However, in the secondary treatment balloon assembly 250 of FIG. 2E, there can be included a connector or locking mechanism 240, such as a suitable luer lock, that can include suitable male or female connectors to selectively connect the secondary treatment balloon assembly 250 to the catheter 600.

The connector or locking mechanism 240 or a portion thereof can be integrally formed with or suitably connected with the distal end portion 216 of the catheter 600 at an area 241, such as with a suitable glue or adhesive, for example. Also, the connector or locking mechanism 240 or a portion thereof can be integrally formed with or suitably connected with the proximal end of the neck area 257 of the secondary treatment balloon assembly 250 at the area 241, such as with a suitable glue or adhesive. Such connector or locking mechanism 240 can assist in enabling attaching or exchanging with the catheter 600 various sizes and configurations of the secondary treatment balloon assembly 250 at the area 241 to facilitate treatment and treatment options, for example. Further, in FIG. 2E, the inner secondary treatment balloon 254 only includes the first secondary treatment lumen 256 and the connector 255a, with the second secondary treatment lumen 258 and the connector 255b being optionally indicated by dashed lines therein.

Also, in the secondary treatment balloon assembly 250 illustrated and described with respect to FIGS. 2C, 2D and 2E, the lumens 201a, 202a and 213a can also be extended through the neck area 257 by one or more a suitable connector lumens, that can be integrally formed or joined therewith by a suitable process or method, to respectively communicate with such corresponding connector lumens in the neck area 257 that can correspondingly communicatively connect or communicatively associate the lumens 201a, 202a and 213a with the connectors 255a, 255b, the inner secondary treatment balloon 254, the outer secondary treatment balloon 252, the first secondary treatment lumen 256 and the second secondary treatment lumen 258, as described.

Figure 2F:
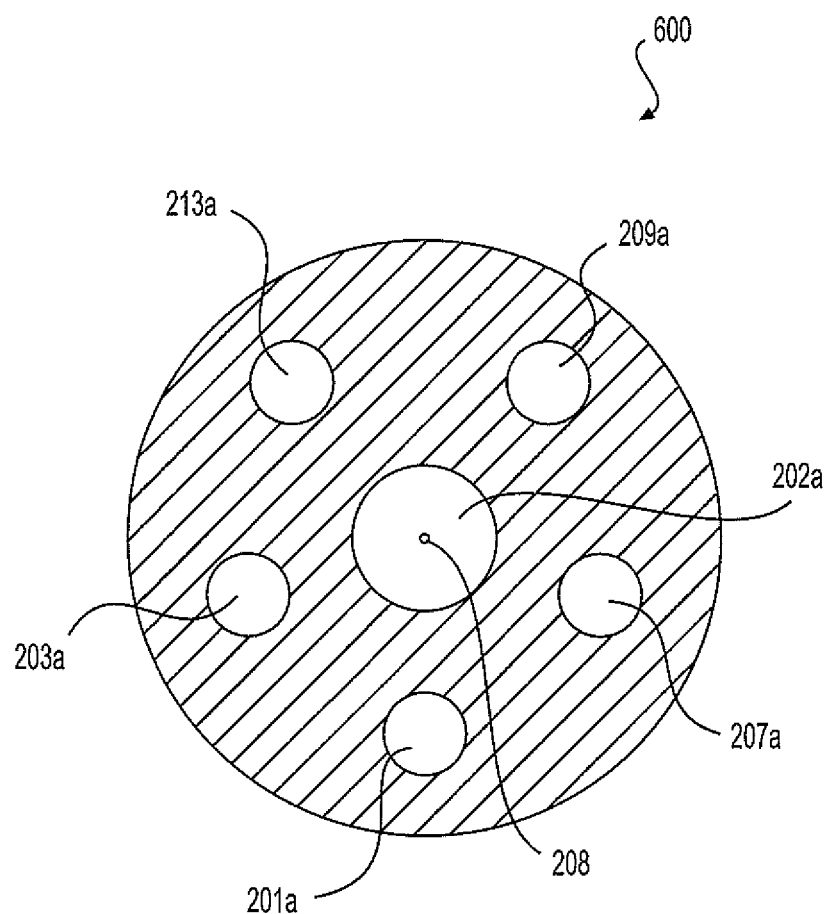
FIG. 2F is a cross-sectional view taken along lines 2F-2F of FIG. 2C.

Referring now to FIG. 2F, there is illustrated a cross-sectional planar view taken along the 2F-2F plane of the catheter 600 of FIG. 2C. The catheter 600 is illustrated in section in FIG. 2F along with relative positions of the lumens 201a, 202a, 203a, 207a, 209a and 213a, for example. Also, FIG. 2F illustrates a relative position of the radioactive wire 208 within the lumen 202a. The central lumen 202a allows for selectively inserting and positioning the radioactive wire, such as the radioactive wire 208, or for selectively providing other suitable treatment mediums, for delivery of the medical treatment, for example.

While various embodiments of inflatable balloons of embodiments of the multi-purpose balloon catheters described herein have been associated with a single spiral or a circular treatment lumen or a single treatment lumen, or associated with first and second treatment lumens, positioned in association with a distal inflatable balloon of the catheter, embodiments of distal inflatable balloons for delivery of treatment should not be construed a to be so limiting. In this regard, a distal inflatable balloon for treatment can include a relatively large number of treatment lumens associated with a corresponding distal inflatable balloon. For example, a distal inflatable balloon for the delivery of a medical treatment can include one to fifteen treatment lumens associated with or attached to a distal inflatable balloon, desirably attached to or associated with an inner wall or inner surface of the balloon or attached to or associated with an inner balloon of a distal inflatable balloon.

Such multiple treatment lumens associated with a distal inflatable balloon can be selectively used for the delivery of a plurality of treatments, procedures, or other therapeutic purposes, such as for the delivery of radiation therapy, delivery of contrast agents for imaging or mapping a location, delivery of various therapeutic agents, etc., for example, using a single distal balloon associated with a catheter, similar to those described herein. For example, a distal inflatable balloon associated with a catheter for treatment or a related procedure desirably can include five such treatment lumens, such as one treatment lumen being positioned at a center of an inner treatment balloon and four treatment lumens positioned in association with the periphery of the inner treatment balloon.

It is to be understood that the present invention is not limited to the embodiments described above, but encompasses any and all embodiments within the scope of the following claims.

I claim:

1. A multi-purpose balloon catheter for a medical treatment, comprising:
   a single intra-cavity catheter configured for insertion into a body cavity for the medical treatment, the single intra-cavity catheter having a proximal end portion, a central portion and a non-branching distal end portion;
   a plurality of lumens positioned in association with the single intra-cavity catheter extending from the proximal end portion of the single intra-cavity catheter, wherein the plurality of lumens including a central lumen coaxially positioned within a larger main lumen extending longitudinally through the single intra-cavity catheter to the non-branching distal end portion;
   a plurality of independent and distinct balloon groups positioned in association with the central portion of the single intra-cavity catheter, each independent and distinct balloon group being independently spaced from each other independent and distinct balloon group on the single intra-cavity catheter, each independent and distinct balloon group is positioned in a non-overlapping contiguous arrangement on a same longitudinal axis of the single intra-cavity catheter, each independent and distinct balloon group including at least one inflatable balloon, and each independent and distinct balloon group being communicatively associated with a corresponding at least one of the plurality of lumens;
   an applicator extender communicatively associated with the non-branching distal end portion of the single intra-cavity catheter, the applicator extender being configured to be in communication with the central lumen for delivering the medical treatment; and
   a secondary treatment balloon configured to be communicatively connected with the applicator extender and configured to be in communication with a corresponding at least one other of the plurality of lumens.

2. The multi-purpose balloon catheter according to claim 1, further comprising:
   a plurality of connectors positioned in association with the proximal end portion of the single intra-cavity catheter, each of the plurality of connectors being respectively communicatively connected with a corresponding at least one of the plurality of lumens, each of the plurality of connectors being configured to enable respectively selectively receiving or removing through a corresponding lumen one or more of a liquid saline solution, a fluid medium, a gaseous medium, a contrast medium, a radioactive material or other treatment medium for the medical treatment.

3. The multi-purpose balloon catheter according to claim 1, wherein:
   the body cavity for the medical treatment is selected from the group consisting of an esophagus, a rectum, a vagina and a surgically created cavity.

4. The multi-purpose balloon catheter according to claim 1, wherein:
   the catheter comprises polyurethane.

5. The multi-purpose balloon catheter according to claim 1, wherein:
   the at least one inflatable balloon in each of the plurality of balloon groups has a shape selected from the group consisting of a cylindrical shape, a rectangular shape, an oval shape and a spherical shape.

6. The multi-purpose balloon catheter according to claim 1, wherein:
   the at least one inflatable balloon in each of the plurality of balloon groups is made of a material selected from the group consisting of nylon, polyurethane, polyether block amide, and polyethylene terephthalate or a combination thereof.

7. The multi-purpose balloon catheter according to claim 1, wherein:
   at least one portion of the multi-purpose balloon catheter or the at least one inflatable balloon in at least one of the plurality of independent and distinct balloon groups is coated with a medicinal agent for releasing the medicinal agent internally to a predetermined location in the body cavity in association with or for the medical treatment.

8. The multi-purpose balloon catheter according to claim 1, wherein: the applicator extender includes at least one chamber and at least one of a membrane or a gate member positioned in association with the at least one chamber of the applicator extender, the at least one of the membrane or the gate member being configured to enable passage of the central lumen through to the secondary treatment balloon, the central lumen configured to one or more of selectively provide the secondary treatment balloon with at least one of a radioactive material, a treatment medium, a contrast medium or a therapeutic agent for the delivery of the medical treatment or enable selectively inflating and deflating the secondary treatment balloon to one or more of selectively position or stabilize the secondary treatment balloon for the medical treatment.

9. The multi-purpose balloon catheter according to claim 1, wherein:
   the applicator extender includes at least one connector configured to selectively communicatively associate the applicator extender with the non-branching distal end portion of the single intra-cavity catheter.

10. The multi-purpose balloon catheter according to claim 1, wherein:
at least one of the plurality of lumens is configured to receive a radioactive material for the medical treatment.

11. The multi-purpose balloon catheter according to claim 10, wherein: the radioactive material includes at least one of a radioactive wire or a radioactive seed.

12. The multi-purpose balloon catheter according to claim 10, wherein:
the radioactive material is selected from the group consisting of Ir-192, Au-198, I-125 and Cs-131.

13. The multi-purpose balloon catheter according to claim 12, wherein:
the radioactive material delivers a dose of radiation ranging from 1 Curie to 10 Curies.

14. A multi-purpose balloon catheter for a medical treatment, comprising:
a single intra-cavity catheter configured for insertion into a body cavity for the medical treatment, the single intra-cavity catheter having a proximal end portion, a central portion and a non-branching distal end portion;
a plurality of lumens positioned in association with the single intra-cavity catheter extending from the proximal end portion of the single intra-cavity catheter, wherein the plurality of lumens including a central lumen coaxially positioned within a larger main lumen extending longitudinally through the single intra-cavity catheter to the non-branching distal end portion;
a plurality of independent and distinct balloon groups positioned in association with the central portion of the single intra-cavity catheter, each independent and distinct balloon group being independently spaced from each other independent and distinct balloon group on the single intra-cavity catheter, each independent and distinct balloon group is positioned in a non-overlapping contiguous arrangement on a same longitudinal axis of the single intra-cavity catheter, each independent and distinct balloon group including at least one inflatable balloon, and each independent and distinct balloon group being communicatively associated with a corresponding at least one of the plurality of lumens;
an applicator extender communicatively associated with the non-branching distal end portion of the single intra-cavity catheter, the applicator extender being configured to be in communication with the central lumen for delivering the medical treatment; and
a secondary treatment balloon configured to be communicatively connected with the applicator extender and configured to be in communication with a corresponding at least one of the plurality of lumens in communication with the applicator extender, at least one of the plurality of lumens being configured to selectively provide to the secondary treatment balloon at least one of a radioactive material, a treatment medium, a contrast medium or a therapeutic agent for the medical treatment or enable selectively inflating or deflating the secondary treatment balloon to one or more of selectively position or stabilize the secondary treatment balloon for the medical treatment.

15. The multi-purpose balloon catheter according to claim 14, further comprising:
a plurality of connectors positioned in association with the proximal end portion of the single intra-cavity catheter, each of the plurality of connectors being respectively communicatively connected with a corresponding at least one of the plurality of lumens, the plurality of connectors being configured to enable respectively selectively receiving or removing through a corresponding one of the plurality of lumens one or more of a liquid saline solution, a fluid medium, a gaseous medium, the contrast medium, the radioactive material, the therapeutic agent or the treatment medium for the medical treatment.

16. The multi-purpose balloon catheter according to claim 14, wherein:
the applicator extender includes at least one chamber and at least one of a membrane or a gate member positioned adjacent to the at least one chamber of the applicator extender, the at least one of the membrane or the gate member being configured to selectively pass through the central lumen in communication with the applicator extender to the secondary treatment balloon at least one of the radioactive material, the treatment medium, the contrast medium or the therapeutic agent for delivering the medical treatment or enable selectively inflating and deflating the secondary treatment balloon to one or more of selectively position or stabilize the secondary treatment balloon for the medical treatment.

17. The multi-purpose balloon catheter according to claim 14, wherein:
the applicator extender includes at least one connector configured to selectively communicatively associate the applicator extender with the non-branching distal end portion of the single intra-cavity catheter.

18. A multi-purpose balloon intra cavity catheter for a medical treatment, comprising:
a single intra-cavity catheter configured for insertion into a body cavity for the medical treatment, the single intra-cavity catheter having a proximal end portion, a central portion and a non-branching distal end portion;
a plurality of lumens positioned in association with the single intra-cavity catheter extending from the proximal end portion of the single intra-cavity catheter, wherein the plurality of lumens including a central lumen coaxially positioned within a larger main lumen extending longitudinally through the single intra-cavity catheter to the non-branching distal end portion;
a plurality of independent and distinct balloon groups positioned in association with the central portion of the single intra-cavity catheter, each independent and distinct balloon group being independently spaced from each other independent and distinct balloon group on the single intra-cavity catheter, each independent and distinct balloon group is positioned in a non-overlapping contiguous arrangement on a same longitudinal axis of the single intra-cavity catheter, each independent and distinct balloon group including at least one inflatable balloon, and each independent and distinct balloon group being communicatively associated with a corresponding at least one of the plurality of lumens, wherein at least one of the plurality of independent and distinct balloon groups is configured to be selectively inflated or deflated to selectively position the single intra-cavity catheter in the body cavity for the medical treatment, and at least one other of the plurality of independent and distinct balloon groups is configured to receive at least one of a treatment medium, a radioactive material, a therapeutic agent or a contrast medium for the medical treatment;
an applicator extender communicatively associated with the non-branching distal end portion of the single intra-cavity catheter, the applicator extender including at least one chamber and further including at least one of a membrane or a gate member positioned adjacent to the at least one chamber, the at least one of the membrane or the gate member being configured to receive and to selectively provide via the central lumen in communication with the applicator extender at least one of the radioactive material, the treatment medium, the contrast medium or the therapeutic agent for delivering the medical treatment; and a secondary treatment balloon configured to be communicatively connected with the applicator extender and configured to be in communication with a corresponding at least one of the plurality of lumens in communication with the applicator extender, at least one of the plurality of lumens in communication with the applicator extender configured to one or more of respectively receive to selectively provide the secondary treatment balloon with at least one of the radioactive material, the treatment medium, the contrast medium or the therapeutic agent for the medical treatment or enable selectively inflating or deflating the secondary treatment balloon to one or more of selectively position or stabilize the secondary treatment balloon for the medical treatment.

19. The multi-purpose balloon catheter according to claim 18, wherein:

the radioactive material is selected from the group consisting of Ir-192, Au-198, I-125 and Cs-131.

20. The multi-purpose balloon catheter according to claim 19, wherein:

the radioactive material delivers a dose of radiation ranging from 1 Curie to 10 Curies.

* * * * *